US012697618B2

(12) United States Patent
Wang et al.

(10) Patent No.: US 12,697,618 B2
(45) Date of Patent: Aug. 4, 2026

(54) METHODS AND RELATED ASPECTS FOR MULTIPLEXED ANALYTE DETECTION USING SEQUENTIAL MAGNETIC PARTICLE ELUTION

(71) Applicant: THE JOHNS HOPKINS UNIVERSITY, Baltimore, MD (US)

(72) Inventors: Tza-Huei Jeff Wang, Germantown, MD (US); Alexander Y. Trick, Baltimore, MD (US); Fan-En Chen, Baltimore, MD (US); Liben Chen, Ellicott City, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 498 days.

(21) Appl. No.: 18/263,010

(22) PCT Filed: Jan. 28, 2022

(86) PCT No.: PCT/US2022/014220
§ 371 (c)(1),
(2) Date: Jul. 26, 2023

(87) PCT Pub. No.: WO2022/165113
PCT Pub. Date: Aug. 4, 2022

(65) Prior Publication Data
US 2024/0123447 A1      Apr. 18, 2024

Related U.S. Application Data

(60) Provisional application No. 63/143,624, filed on Jan. 29, 2021.

(51) Int. Cl.
*B01L 3/00* (2006.01)
*G01N 33/543* (2006.01)

(52) U.S. Cl.
CPC .. *B01L 3/502761* (2013.01); *G01N 33/54326* (2013.01); *B01L 2200/027* (2013.01);
(Continued)

(58) Field of Classification Search
CPC ....... B01L 2200/027; B01L 2200/0631; B01L 2200/0647; B01L 2200/0689;
(Continued)

(56) References Cited

U.S. PATENT DOCUMENTS

2010/0209927 A1      8/2010  Menon et al.
2019/0383841 A1*    12/2019  Feitsma ............. G01N 30/6078

FOREIGN PATENT DOCUMENTS

WO        2016154038 A1        9/2016
WO        2019213096 A1        11/2019
WO        2021243080 A1        12/2021

OTHER PUBLICATIONS

International Search Report and Written Opinion in corresponding International Application No. PCT/US2022/014220 mailed on Apr. 21, 2022, 14 pages.
(Continued)

*Primary Examiner* — Jennifer Wecker
*Assistant Examiner* — Jonathan Bortoli
(74) *Attorney, Agent, or Firm* — MH2 Technology Law Group LLP

(57)        ABSTRACT

Provided herein are magnetofluidic cartridges of use in a wide variety of sample analysis applications, including nucleic acid amplification assays. The magnetofluidic cartridges include sample inlet wells and sample analysis wells for performing controlled serial elution techniques that enables execution of extraction/purification and splitting of analytes for multiplex detection via magnetic actuation only.
(Continued)

Related magnetofluidic devices, kits, and methods are also provided.

6 Claims, 14 Drawing Sheets

Specification includes a Sequence Listing.

(52) U.S. Cl.
CPC .................. *B01L 2200/0647* (2013.01); *B01L 2200/0689* (2013.01); *B01L 2200/10* (2013.01); *B01L 2200/16* (2013.01); *B01L 2300/12* (2013.01); *B01L 2400/043* (2013.01)

(58) Field of Classification Search
CPC ............. B01L 2200/10; B01L 2200/16; B01L 2300/0816; B01L 2300/0864; B01L 2300/12; B01L 2300/1805; B01L 2400/043; B01L 2400/0677; B01L 3/502761; B01L 3/50851; B01L 7/52; G01N 33/54326; G01N 33/54366; G01N 35/0098
See application file for complete search history.

(56) References Cited

OTHER PUBLICATIONS

Abi-Samra, K. et al. "Infrared controlled waxes for liquid handling and storage on a CD-microfluidic platform." Lab on a Chip 11.4 (2011): 723-726.
International Preliminary Report on Patentability in corresponding International Application No. PCT/US2022/014220 mailed on Aug. 10, 2023, 10 pages.
Extended European Search Report in corresponding European Application No. 22746654.7 mailed on Dec. 9, 2024, 8 pages.

* cited by examiner

| Set # | Elution condition | | Elution efficiency (%) |
|---|---|---|---|
| 1 | 1st | 50 C 10sec | 8.22 |
| | 2nd | 60 C 2min | 29.96 |
| 2 | 1st | 60 C 2min | 40.92 |
| | 2nd | 50 C 10sec | 11.56 |
| 3 | 1st | 50 C 10sec | 7.98 |
| | 2nd | 50 C 10sec | 7.06 |
| 4 | 1st | 60 C 2min | 39.75 |
| | 2nd | 60 C 2min | 39.75 |
| 5 | 1st | 50 C 1min | 14.91 |
| | 2nd | 50 C 1min | 10.22 |

B

METHODS AND RELATED ASPECTS FOR MULTIPLEXED ANALYTE DETECTION USING SEQUENTIAL MAGNETIC PARTICLE ELUTION

CROSS-REFERENCE TO RELATED APPLICATIONS

This application is the national stage entry of International Patent Application No. PCT/US2022/014220, filed on Jan. 28, 2022, and published as WO 2022/165113 A1 on Aug. 4, 2022, which claims the benefit of U.S. Provisional Patent Application Ser. No. 63/143,624, filed Jan. 29, 2021, both of which are hereby incorporated by reference herein in their entireties.

STATEMENT REGARDING FEDERALLY SPONSORED RESEARCH OR DEVELOPMENT

This invention was made with government support under grant AI138978 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 27, 2022, is named 0184_0138-PCT_SL.txt and is 6,216 bytes in size.

BACKGROUND

Multiplexed detection in chemical and biochemical assays, in which multiple analytes are detected from a single sample, is an important feature for in vitro diagnostics. The demand for multiplexed detection stems from the importance of simultaneously detecting multiple infectious agents that could cause the host a similar clinical symptoms, detecting internal controls to ensure an assay is performing properly, or assessing expression of multiple biomarkers for disease diagnosis and genotyping of plants or animals. However, current methods for multiplexed detection of analytes are limited by laborious manual processes or use fluidic handling instruments that are too large, complex, or expensive for widespread adoption.

Directly detecting analytes in a crude sample may risk assay failure or interference due to the presence of inhibitory or competing compounds, and dilute samples may result in low sensitivity of the assay, so typical biochemical assays first require concentrating and purifying analytes. This purification may be implemented using a substrate such as functionalized particles/beads, spin columns, or filters, followed by washing and elution of the analytes and subsequent dispensing with assay reagents. Purified analytes may be detected with the use of electrochemical, fluorescent or colorimetric labels in separate biochemical reactions or within a single reaction for simultaneously measuring multiple analytes. Multiplexing assays in a single reaction volume can result in assay competition and cross-talk which potentially reduces sensitivity or results in false positives, so if possible splitting the sample into multiple reactions with minimal multiplexing is desired to maintain sensitivity and specificity of the assays. Conventionally, analyte purification and splitting are discrete processes requiring different modalities of operation. The process of purification relies on a solid phase for analyte binding, wash and elution, while splitting is carried out on a liquid phase by aliquoting the elute containing purified analytes. Integration of these two steps in an automated manner requires the incorporation of various actuations mechanisms (mechanical, magnetic and fluidic) that cannot be implemented without bulky and costly instrumentation.

Accordingly, there is a need for additional methods, and related aspects, for more simplified multiplexed analyte detection.

SUMMARY

The present disclosure relates, in certain aspects, to methods that provide a streamlined workflow for combining analyte purification and aliquoting for achieving highly multiplexed biochemical reactions that can be implemented for automation in a compact and miniaturized instrument. Using analyte binding onto functionalized magnetic particles followed by sequential partial elution off the magnetic particles, analytes from a single sample can be directly eluted into a series of assay reagents. The direct elution off the particles into assays removes the need for precision liquid dispensing or additional dilution in an elution buffer. Furthermore, the amount of analyte released in each elution step is tunable by controlling the elution conditions such as temperature, time and buffer condition (pH, salt concentrations, etc.). This controlled serial elution technique enables execution of extraction/purification and splitting of analytes for multiplex detection via magnetic actuation only. This integrated analyte preparation and multiplexing strategy is readily amenable for integration into, for example, various magnetofluidic cartridges for rapid, automated, and affordable diagnostics. The proposed multielution strategy can also be automated for a larger scale use by integrating into automatic liquid handling system. These and other aspects will be apparent upon a complete review of the present disclosure, including the accompanying figures.

In another aspect, the present disclosure provides a method of detecting multiple biomolecules in a sample. The method includes contacting at least an aliquot of the sample that comprises the multiple biomolecules with a plurality of magnetic particles in a sample inlet well of a magnetofluidic cartridge, as described herein, under conditions such that at least first and second biomolecules in the aliquot bind to the plurality of magnetic particles to produce bound biomolecules. The method also includes moving the bound biomolecules from the sample inlet well to a first sample analysis well of the magnetofluidic cartridge that fluidly communicates with the sample inlet well using at least one magnet and eluting at least some of the first biomolecules from the plurality of magnetic particles in the first sample analysis well under at least a first set of elution conditions to produce unbound first biomolecules in the first sample analysis well. The method also includes moving the bound biomolecules from the first sample analysis well to a second sample analysis well of the magnetofluidic cartridge that fluidly communicates with the first sample analysis well using the magnet and eluting at least some of the second biomolecules from the plurality of magnetic particles in the second sample analysis well under at least a second set of elution conditions to produce unbound second biomolecules in the second sample analysis well. In addition, the method also includes detecting the unbound first biomolecules and/or molecules derived therefrom (e.g., an amplicon or the like) in the first sample analysis well and the unbound second biomolecules and/or molecules derived therefrom (e.g., an amplicon or the like) in the second sample analysis well (e.g., while performing a nucleic acid amplification reaction and/or a protein analysis assay in the sample analysis wells), thereby detecting the multiple biomolecules in the sample. In some embodiments, the method also includes washing the bound biomolecules prior to eluting the first and/or second biomolecules from the plurality of magnetic particles. In some embodiments, the method also includes tuning one or more of the elution conditions. Typically, the elution conditions comprise one or more independently defined parameters selected from, for example, a temperature, a duration, a buffer composition, a reaction mixture composition, a pH level, and/or the like. In some embodiments, the first and second biomolecules comprise different loci of a genomic DNA or different variants of an identical genetic locus.

In one aspect, the present disclosure provides a magnetofluidic cartridge that includes a body structure comprising at least one sample inlet well and a plurality of sample analysis wells that fluidly communicate with one another. Each of the plurality of sample analysis wells comprises a processing reagent and is configured to undergo a set of tunable elution conditions during operation of a magnetofluidic device when a cartridge assembly of the magnetofluidic device accepts and secures the magnetofluidic cartridge and when the magnetofluidic device moves substantially only magnetic particles comprising bound biomolecules among the wells. That is, the magnetofluidic device typically lacks a fluid conveyance mechanism operable to effect conveyance of fluidic materials in the magnetofluidic cartridge. In some embodiments, each of the plurality of sample analysis wells comprises a different processing reagent. In some embodiments, each of the plurality of sample analysis wells is configured to undergo a different set of tunable elution conditions. In some embodiments, the body structure further comprises at least one sample washing well that fluidly communicates with the sample inlet well and the plurality of sample analysis wells. In some embodiments, a sealing fluid disposed in at least a portion of the body structure, which sealing fluid is immiscible with the processing reagents such that the processing reagents are substantially contained within the sample analysis wells. In some embodiments, the magnetofluidic cartridge described herein comprise 3, 4, 5, 6, 7, 8, 9, 10, or more sample analysis wells (e.g., for performing even higher multiplexed analyses).

In one aspect, the present disclosure provides a magnetofluidic cartridge that includes a top layer, a bottom layer spaced apart from the top layer in a generally parallel orientation with respect to the top layer, which bottom layer defines a plurality of wells that protrude from a surface of the bottom layer, wherein the plurality of wells comprises at least one sample inlet well and at least two sample analysis wells, which sample analysis wells are configured to undergo a set of tunable elution conditions. The magnetofluidic cartridge also includes a spacer layer operably connected to the top and bottom layers, a channel defined by the top, bottom, and spacer layers, which channel is capable of fluidily communicating with the plurality of wells, and at least one port disposed through the top layer and at least proximal to the sample inlet well, which port fluidily communicates with the channel. The magnetofluidic cartridge also includes a sealing mechanism (e.g., a lid, a cap, or the like) operably connected, or connectable, to at least the top layer, which sealing mechanism seals the port when the sealing mechanism is in a closed position, a plurality of magnetic particles disposed in at least the sample inlet well, and processing reagents (e.g., at least some reagents of a nucleic acid amplification reaction mixture) disposed in each of the sample analysis wells. In some embodiments, the magnetofluidic cartridge also includes a first temperature sensitive material disposed in a substantially solid state in the channel between the sample inlet well and the sample analysis well, which first temperature sensitive material fluidly partitions the sample inlet well and the sample analysis well from one another when the first temperature sensitive material is in the substantially solid state to produce a first region that comprises the sample inlet well and at least a first portion of the channel and a second region that comprises the sample analysis wells and at least a second portion of the channel, and a sealing fluid disposed at least in the second portion of the channel of the second region, which sealing fluid is immiscible with the processing reagents such that the processing reagents are substantially contained within the sample analysis wells. In some aspects, the present disclosure provides a kit that includes the magnetofluidic cartridge disclosed herein.

In another aspect, the present disclosure provides a magnetofluidic device that includes a cartridge assembly structured to accept and secure the magnetofluidic cartridge as described herein. The magnetofluidic device also includes a temperature modulation assembly arranged proximate to the cartridge assembly, which temperature modulation assembly comprises at least one heat source that selectively thermally communicates with one or more of the plurality of wells and/or the channel of the magnetofluidic cartridge. In some embodiments, for example, a temperature modulation assembly includes a thermoelectric element, a resistive heater, a heated air element, an electromagnetic radiation, and/or the like. The magnetofluidic device also includes a magnetic particle manipulation assembly arranged proximate to the cartridge assembly, which magnetic particle manipulation assembly comprises a pair of magnets arranged to be on opposing sides of the magnetofluidic cartridge and which are substantially aligned along a line that will be transverse to the magnetofluidic cartridge such that the line can be aligned with one or more of the plurality of wells in the magnetofluidic cartridge. The pair of magnets are moveable along the line relative to the magnetofluidic cartridge, or a strength of the pair of magnets is adjustable such that the plurality of magnetic particles when contained within the one or more wells can be drawn out of and back into the one or more wells during operation. Typically, the magnetofluidic device lacks a fluid conveyance mechanism operable to effect conveyance of fluidic materials in the magnetofluidic cartridge.

The magnetofluidic cartridges disclosed herein include various embodiments. In some embodiments, for example, the first temperature sensitive material is insoluble in aqueous materials; less dense than at least the plurality of magnetic particles and the sealing fluid; less dense than a sample and assay reagents; in the substantially solid state at a temperature less than about 40° C.; and/or in at least a partially fluid state at a temperature more than about 40° C.

In certain embodiments, the first temperature sensitive material is wax. In some embodiments, the wax is selected from the group consisting of: a higher alkane (e.g., docosane or the like), a paraffin wax, a beeswax, a carnauba wax, a candelilla wax, and a ceresin wax. In some embodiments, the sealing fluid is a hydrophobic fluid.

In some embodiments, the magnetic particles comprise a plurality of magnetic beads. In certain embodiments, the magnetic particles comprise a plurality of magnetic nanoparticles. In some of these embodiments, for example, the plurality of magnetic particles is coated magnetic nanoparticles that are coated with a coating material that electrostatically binds nucleic acids.

In certain embodiments, at least one of the plurality of wells comprises a wall sufficiently thin to allow a heat transfer rate such that a nucleic acid amplification assay can be completed in less than 20 minutes. In some of these embodiments, a wall of at least one of the plurality of wells comprises a thickness of between about 0.05 mm and about 0.5 mm.

In some embodiments, the processing reagents are lyophilized. In certain embodiments, the processing reagents comprise nucleic acid amplification reaction mixtures. In some embodiments, the magnetofluidic cartridge further includes a second temperature sensitive material disposed in a substantially solid state at least proximal to one or more of the sample analysis wells, which second temperature sensitive material fluidly partitions the processing reagents disposed in the one or more sample analysis wells and the sealing fluid disposed in the second portion of the channel of the second region from one another when the second temperature sensitive material is in the substantially solid state. In certain embodiments, for example, the second temperature sensitive material coats the processing reagent. In some of these embodiments, the magnetofluidic cartridge further includes at least one reconstitution buffer disposed in at least one of the sample analysis wells, wherein the second temperature sensitive material separates the reconstitution buffer from at least one of the processing reagents.

In certain embodiments, the bottom layer further defines at least one sample washing well that protrudes from the surface of the bottom layer and fluidly communicates with the second portion of the channel of the second region. In some of these embodiments, the magnetofluidic cartridge also includes at least one washing buffer disposed in at least the sample washing well.

In some embodiments, the sealing fluid comprises a silicone oil. In certain embodiments, the plurality of magnetic particles is in a dried state. In some of these embodiments, for example, the plurality of magnetic particles is lyophilized. In some embodiments, the magnetofluidic cartridge also includes at least one control reagent disposed in one or more of the wells, which control reagent is in a dried state. In certain of these embodiments, for example, the control reagent is lyophilized. In certain embodiments, the magnetofluidic cartridge also includes at least one sample comprising the biomolecules disposed in the sample inlet well. In some of these embodiments, the biomolecule comprises at least one nucleic acid (e.g., DNA and/or RNA) and/or at least one protein or fragments thereof (e.g., antibodies, antigens, and/or the like). In certain embodiments, the magnetofluidic cartridge also includes at least one buffer, at least one salt, and/or at least one lytic reagent (e.g., a detergent, a surfactant, a chaotrope, an enzyme, and/or the like) disposed in one or more of the wells. In some embodiments, pH/salt conditions are adjusted to alter binding properties of the plurality of magnetic particles. In certain embodiments, lytic reagents are used to neutralize the activity of various sample components, lyse cells, disrupt viral envelopes, and/or the like.

BRIEF DESCRIPTION OF THE DRAWINGS

The accompanying drawings, which are incorporated in and constitute a part of this specification, illustrate certain embodiments, and together with the written description, serve to explain certain principles of the methods, devices, kits, and systems disclosed herein. The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

DEFINITIONS

Figure 1A:
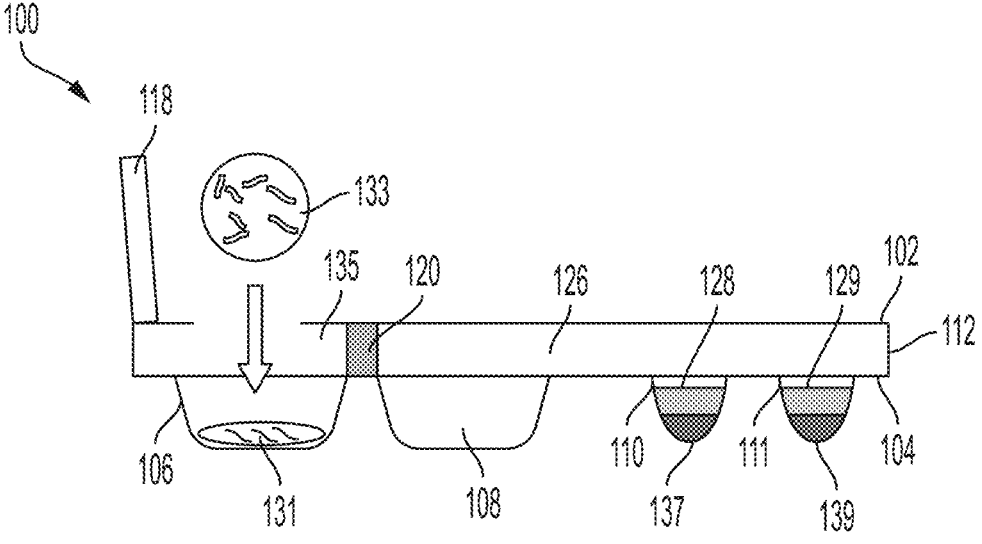
FIGS. 1A and B schematically show a magnetofluidic cartridge from side and top views according to one exemplary embodiment.
Figure 1B:
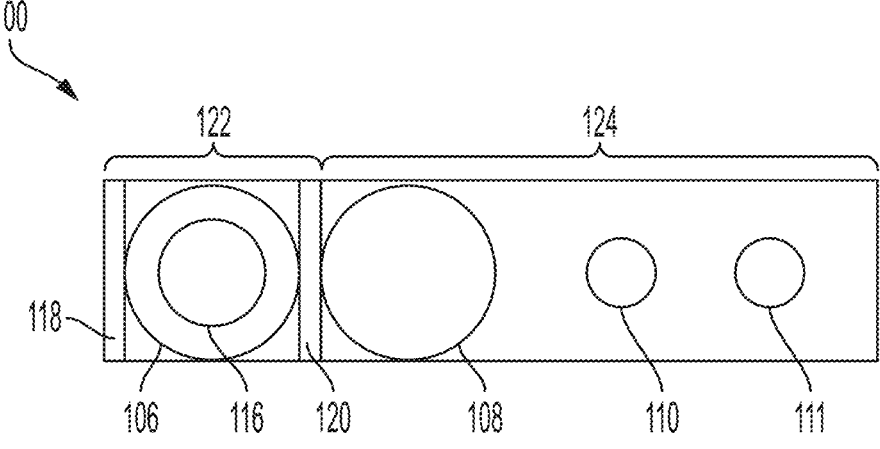

In order for the present disclosure to be more readily understood, certain terms are first defined below. Additional definitions for the following terms and other terms may be set forth throughout the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

It is also to be understood that the terminology used herein is for the purpose of describing particular embodiments only and is not intended to be limiting. Further, unless defined otherwise, all technical and scientific terms used herein have the same meaning as commonly understood by one of ordinary skill in the art to which this disclosure pertains. In describing and claiming the methods, magnetofluidic cartridges, magenetofluidic devices or systems, and component parts, the following terminology, and grammatical variants thereof, will be used in accordance with the definitions set forth below.

About: As used herein, "about" or "approximately" or "substantially" as applied to one or more values or elements of interest, refers to a value or element that is similar to a stated reference value or element. In certain embodiments, the term "about" or "approximately" or "substantially" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Amplifying: As used herein, "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. Amplification is not limited to the strict duplication of the starting molecule. For example, the generation of multiple cDNA molecules from a limited amount of RNA in a sample using RT-PCR is a form of amplification. Furthermore, the generation of multiple RNA molecules from a single DNA molecule during the process of transcription is also a form of amplification.

Biomolecule: As used herein, "biomolecule" refers to an organic molecule produced by a living organism. Examples of biomolecules, include macromolecules, such as nucleic acids, proteins, carbohydrates, and lipids.

Detect: As used herein, "detect," "detecting," or "detection" refers to an act of determining the existence or presence of one or more target biomolecules (e.g., nucleic acids, proteins, etc.) in a sample.

Mixture: As used herein, "mixture" refers to a combination of two or more different components.

Nucleic Acid: As used herein, "nucleic acid" refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids can also include nucleotide analogs (e.g., bromodeoxyuridine (BrdU)), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA, cfDNA, ctDNA, or any combination thereof.

Protein: As used herein, "protein" or "polypeptide" refers to a polymer of at least two amino acids attached to one another by a peptide bond. Examples of proteins include enzymes, hormones, antibodies, and fragments thereof.

Reaction Mixture: As used herein, "reaction mixture" refers a mixture that comprises molecules that can participate in and/or facilitate a given reaction or assay. To illustrate, a nucleic acid amplification reaction mixture generally includes a solution containing reagents necessary to carry out an amplification reaction, and typically contains primers, a biocatalyst (e.g., a nucleic acid polymerase, a ligase, etc.), dNTPs, and a divalent metal cation in a suitable buffer. A reaction mixture is referred to as complete if it contains all reagents necessary to carry out the reaction, and incomplete if it contains only a subset of the necessary reagents. It will be understood by one of skill in the art that reaction components are routinely stored as separate solutions or in lyophilized forms (e.g., in different wells of a given magnetofluidic cartridge), each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction or assay components.

Sample: As used herein, "sample" means anything capable of being analyzed by the methods, cartridges and/or devices disclosed herein. Samples can include a tissue or organ from a subject; a cell (either within a subject, taken directly from a subject, or a cell maintained in culture or from a cultured cell line); a cell lysate (or lysate fraction) or cell extract; or a solution containing one or more biomolecules derived from a cell or cellular material (e.g., a nucleic acid, a protein, etc.), which is assayed as described herein. A sample may also be any body fluid or excretion (for example, but not limited to, blood, urine, stool, saliva, tears, bile) that contains cells, cell components, or non-cellular fractions. Additional examples of samples include environment and forensic samples. Samples can also include infectious disease agents (e.g., bacteria, viruses, etc.) or plant matter, among other sample types.

DETAILED DESCRIPTION

In general, multiplexed detection in chemical and biochemical assays, in which multiple analytes are detected from a single sample, is an important feature for in vitro diagnostics. The demand for multiplexed detection stems, for example, from the importance of simultaneously detecting multiple infectious agents that could cause the host a similar clinical symptom, detecting internal controls to ensure an assay is performing properly, or assessing expression of multiple biomarkers for disease diagnosis and genotyping of plants or animals. However, previous methods for multiplexed detection of analytes are limited by laborious manual processes or use fluidic handling instruments that are too large, complex, or expensive for widespread adoption.

The present disclosure provides methods and related aspects of a streamlined workflow for combining analyte purification and aliquoting for achieving highly multiplexed biochemical reactions that can be implemented for automation in a compact and miniaturized instrument. Using analyte binding onto functionalized magnetic particles followed by sequential partial elution off the magnetic particles, analytes from a single sample can be directly eluted into a series of assay reagents. The direct elution off the particles into assays removes the need for precision liquid dispensing or additional dilution in an elution buffer. Furthermore, the amount of analyte released in each elution step is tunable by controlling the elution conditions such as temperature, time and buffer condition (pH, salt concentrations, etc.). These controlled serial elution techniques enable execution of extraction/purification and splitting of analytes for multiplex detection via magnetic actuation only. In certain embodiments, this integrated analyte preparation and multiplexing strategy is readily amenable for integration into magnetofluidic cartridges described in, for example, International Publication No. WO2019/213096, U.S. Pat. No. 9,463,461, and U.S. Provisional Patent Application No. 63/031,372, the disclosures of which are incorporated by reference in their entirety. The methods and related aspects are typically implemented at the point-of-need for research and diagnostics in numerous fields including medical molecular tests for infectious diseases or assays for disease detection and/or genotyping in agriculture and livestock, among many other applications. These and other aspects will be apparent upon a complete review of the present disclosure.

To illustrate, FIGS. 1A and B schematically show a magnetofluidic cartridge from side and top views, respectively, according to one exemplary embodiment. As shown, magnetofluidic cartridge 100 includes top layer 102 and bottom layer 104 spaced apart from top layer 102 in a generally parallel orientation with respect to top layer 102. Bottom layer 104 defines a plurality of wells that protrude from a surface of bottom layer 104. In some embodiments, at least one of the plurality of wells comprises a wall sufficiently thin (e.g., a thickness of between about 0.05 mm and about 0.5 mm) to allow a heat transfer rate such that a nucleic acid amplification assay can be completed in less than 20 minutes in magnetofluidic cartridge 100. The plurality of wells includes sample inlet well 106, wash buffer well 108 (e.g., comprising a washing buffer), and sample analysis wells 110 and 111. Magnetic particles 131 (e.g., dried magnetic beads, magnetic nanoparticles, or the like) are disposed in sample inlet well 106. In some embodiments, other reagents such as internal controls are also included in sample inlet well 106. In certain embodiments, magnetic particles are first combined with samples prior to introduction into sample inlet well 106. To further illustrate, magnetic particles are coated magnetic nanoparticles that are coated with a coating material that electrostatically binds nucleic acids or other biomolecules in certain embodiments.

As further shown, processing reagents 137 and 139 are disposed in sample analysis wells 110 and 111, respectively. The compositions of processing reagents 137 and 139 depend on the particular assays to be performed in magnetofluidic cartridge 100. A wide variety of biomolecule detection assays are optionally performed using magnetofluidic cartridge 100. In some embodiments, for example, real-time nucleic acid amplification assays are performed using magnetofluidic cartridge 100. In these embodiments, processing reagents 137 and 139 typically includes independently selected nucleic acid amplification reaction mixture components (e.g., primers, probes, enzymes, nucleotides, etc.). In other exemplary embodiments, immunoassays are performed using magnetofluidic cartridge 100. In these embodiments, processing reagents 137 and 139 typically includes independently selected antibodies, antigens, and/or the like. Exemplary biomolecule detection assays and related upstream sample collection/preparation processes that are optionally adapted for use in the magnetofluidic cartridges disclosed herein are also described in, for example, Shen, *Diagnostic Molecular Biology*, 1st Edition, Academic Press (2019) and Rifai et al., *Principles and Applications of Molecular Diagnostics*, 1st Edition, Elsevier (2018). In some embodiments, processing reagents are disposed in sample analysis well 110 in a dried or lyophilized form, whereas in other embodiments processing reagents are disposed in sample analysis well 110 in a liquid form.

The methods disclosed herein optionally utilize various reaction mixtures that can be used in a wide variety of applications, particularly where it is desirable to determine the fractional abundance of target nucleic acids in amplification reactions. In some embodiments, for example, reaction mixtures are utilized in performing homogeneous amplification/detection assays (e.g., real-time PCR monitoring), or detecting mutations or genotyping nucleic acids. In certain embodiments, multiple primers and/or probes are pooled together in reaction mixtures for use in applications that involve multiplex formats. Many of these applications are described further herein.

In addition to the oligonucleotides (e.g., primers and probes), reaction mixtures also generally include various reagents that are useful in performing, e.g., nucleotide polymerization, nucleic acid amplification and detection reactions (e.g., real-time PCR monitoring or 5'-nuclease assays), and the like. Exemplary types of these other reagents include, e.g., template or target nucleic acids (e.g., obtained or derived from essentially any source), reference nucleic acids, nucleotides, pyrophosphate, light emission modifiers, biocatalysts (e.g., DNA polymerases, RNA polymerases, etc.), buffers, salts, amplicons, glycerol, metal ions (e.g., $Mg^{+2}$, etc.), dimethyl sulfoxide (DMSO), poly rA (e.g., as a carrier nucleic acid for low copy number targets), uracil N-glycosylase (UNG) (e.g., to protect against carry-over contamination). In some kinetic PCR-related applications, reaction mixtures also include probes that facilitate the detection of amplification products. Examples of probes used in these processes include, e.g., hybridization probes, exonuclease probes (e.g., 5'-nuclease probes), and/or hairpin probes.

Magnetofluidic cartridge 100 also includes spacer layer 112 operably connected to top and bottom layers 102 and 104, respectively. Channel 135 is defined by the top, bottom, and spacer layers 102, 104, and 112. As shown, channel 135 is capable of fluidily communicating with the plurality of wells. Magnetofluidic cartridge 100 also includes port 116 disposed through top layer 102 and at least proximal to sample inlet well 106. Port 116 fluidily communicates with channel 135.

As also shown, magnetofluidic cartridge 100 additionally includes sealing mechanism 118 operably connected (via a hinge) to top layer 102. Sealing mechanism 118 seals port 116 when sealing mechanism 118 is in a closed position. In some embodiments, sealing mechanisms are separate caps that are connectable to magnetofluidic cartridge 100. Sample 133 is introduced into sample inlet well 106 via port 116, for example, using a pipette or the like.

In some embodiments, magnetofluidic cartridge 100 optionally also includes first temperature sensitive material 120 disposed in a substantially solid state in channel 135 between sample inlet well 106 and sample analysis well 110. First temperature sensitive material 120 fluidly partitions (e.g., seals) sample inlet well 106 and sample analysis well 110 from one another when first temperature sensitive material 120 is in the substantially solid state to produce first region 122 that comprises sample inlet well 106 and at least a first portion of channel 135 and second region 124 that comprises sample analysis wells 110 and 111, and at least a second portion of channel 135. In addition, magnetofluidic cartridge 100 also optionally includes sealing fluid 126 disposed at least in the second portion of channel 135 of second region 124. Sealing fluid 126 is immiscible with processing reagents 137 and 139 such that processing reagents 137 and 139 are substantially contained within sample analysis wells 110 and 111, respectively. Sealing fluid 126 is typically a hydrophobic fluid, such as silicone oil or the like.

In some embodiments, magnetofluidic cartridge includes temperature sensitive or labile materials at more than one position. For example, magnetofluidic cartridge 100 also includes second temperature sensitive materials 128 and 129 disposed in a substantially solid state at least proximal to sample analysis wells 110 and 111. Second temperature sensitive materials 128 and 129 fluidly partition processing reagents 137 and 139 disposed in sample analysis wells 110 and 111, and sealing fluid 126 disposed in the second portion of channel 135 of second region 124 from one another when second temperature sensitive materials 128 and 129 are in the substantially solid state. In some embodiments, magnetofluidic cartridge 100 also includes comprising at least one reconstitution buffer disposed in sample analysis wells 110 and/or 111. Second temperature sensitive materials 128 and 129 separate the reconstitution buffer from processing reagents 137 and 139 in some of these embodiments.

Many different temperature or temperature labile materials are optionally used in the magnetofluidic cartridge disclosed herein. In some embodiments, for example, temperature sensitive materials (e.g., first temperature sensitive material 120 and/or second temperature sensitive material 128 or 129) are typically insoluble in aqueous materials; less dense than magnetic particles and sealing fluids; in the substantially solid state at a temperature less than about 40° C.; and/or in at least a partially fluid state at a temperature more than about 40° C. In certain embodiments, temperature sensitive materials are a wax, such as a higher alkane (e.g., docosane), a paraffin wax, a beeswax, a carnauba wax, a candelilla wax, a ceresin wax, and/or the like.

Figure 2A:
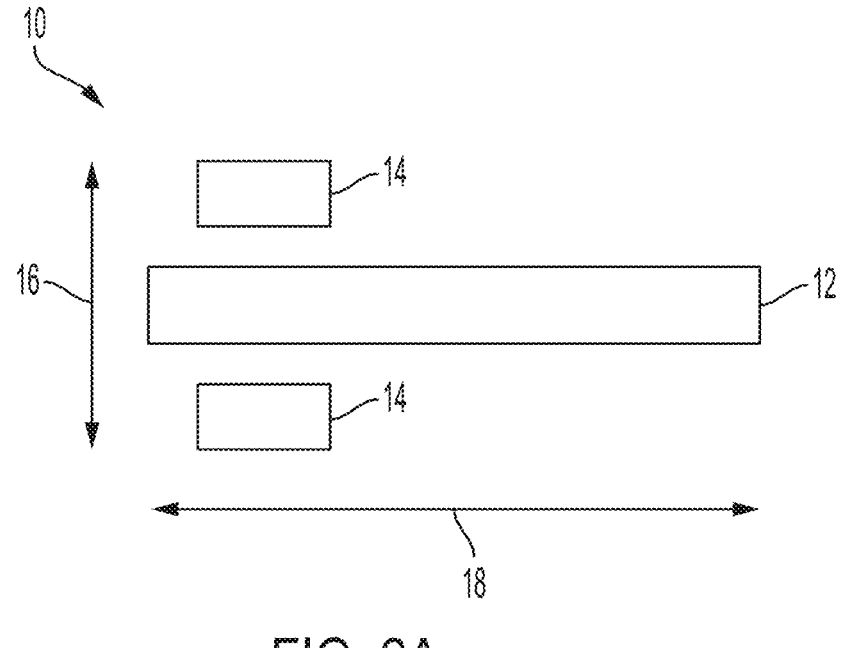
FIG. 2A schematically shows a magnetofluidic device from a side view according to one exemplary embodiment.

FIG. 2A is an illustration of a magnetofluidic device 10 for assaying a biomolecule from a sample according to an embodiment of the present disclosure. The magnetofluidic device of FIG. 2A includes a cartridge assembly 12 structured to accept and secure a magnetofluidic cartridge to be processed and a magnetic particle manipulation assembly 14 arranged proximate the cartridge assembly. The magnetic particle manipulation assembly includes a pair of magnets 14 arranged to be on opposing sides of the magnetofluidic cartridge and substantially aligned along a line 16 that will be transverse to the magnetofluidic cartridge such that the line can be aligned with a well in the magnetofluidic cartridge. In such an embodiment, the pair of magnets 14 are at least one of moveable along the line 16, or a strength of said pair of magnets is adjustable such that a plurality of magnetic particles when contained within the well can be drawn out of and back into the well during operation. In some embodiments, the magnetic particle manipulation assembly 14 is further structured to provide manipulation of the plurality of magnetic particles, after being drawn out of the well, along a second degree of freedom 18 so as to be able to move the plurality of magnetic particles from the well to a second well in the magnetofluidic cartridge.

Figure 2B:
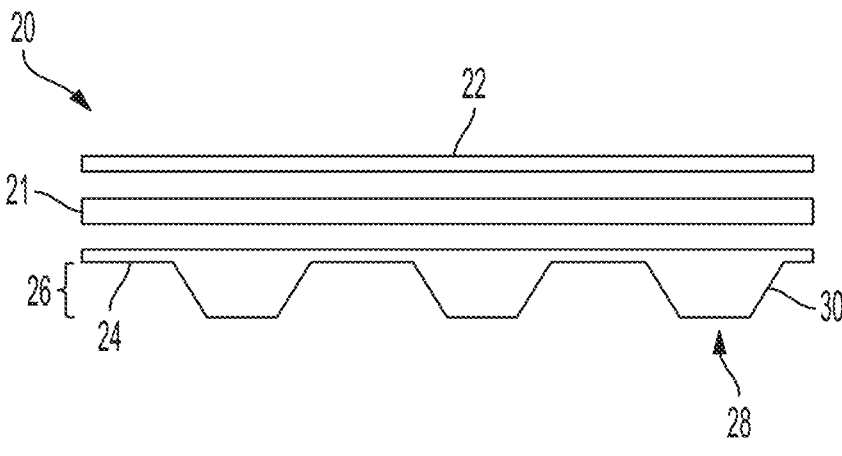
FIG. 2B schematically shows a magnetofluidic cartridge from a side view according to one exemplary embodiment.

FIG. 2B is an illustration showing a magnetofluidic cartridge 20 for assaying biomolecules from a sample according to an embodiment of the present disclosure. The magnetofluidic cartridge of FIG. 2B includes: a top layer 22, a spacer layer 21, and a bottom layer 24 spaced apart from the top layer 22 in a generally parallel orientation with respect to the top layer 22. The bottom layer 24 defines a plurality of wells 26 therein that protrude from a surface of the bottom layer. In such an embodiment, at least one of the plurality of wells 28 has a wall 30 sufficiently thin to facilitate heat transfer such that a nucleic acid amplification assay is completed in under 20 minutes.

Figure 2C:
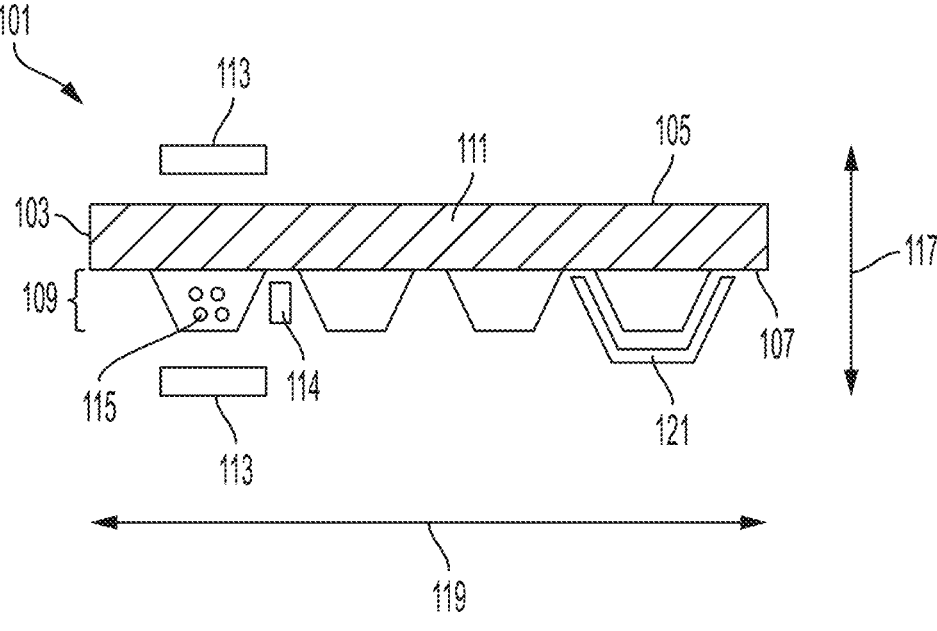
FIG. 2C schematically shows a magnetofluidic device from a side view according to one exemplary embodiment.

FIG. 2C is an illustration of a magnetofluidic device according to an embodiment of the present disclosure. The magnetofluidic device 101 of FIG. 2C includes a magnetofluidic cartridge 103 to be processed contained within a cartridge assembly (not shown) structured to accept and secure a magnetofluidic cartridge to be processed, the magnetofluidic cartridge as described herein having a top layer 105, a bottom layer 107 spaced apart from the top layer in a generally parallel orientation with respect to the top layer, the bottom layer defining a plurality of wells 109 therein that protrude from a surface of the bottom layer; and a spacer layer 111 between and in contact with the top and bottom layers at least along a periphery thereof to seal contents within the magnetofluidic cartridge. The magnetofluidic device also includes a magnetic particle manipulation assembly 113 arranged proximate to the cartridge assembly, the magnetic particle manipulation assembly being structured to provide manipulation of magnetic particles 115 contained within the magnetofluidic cartridge along a first degree of freedom 117 so as to be able to draw magnetic particles into and out of each of the plurality of wells, wherein the magnetic particle manipulation assembly is further structured to provide manipulation of magnetic particles contained within the magnetofluidic cartridge along a second degree of freedom 119 so as to be able to move magnetic particles from one of the plurality of wells to another one of the plurality of wells. The magnetic particle manipulation assembly includes a pair of magnets 113 arranged to be on opposing sides of the magnetofluidic cartridge with one of the plurality of wells therebetween. The magnetofluidic device also includes a temperature control assembly 121 being configured to receive at least one of the plurality of wells. The magnetofluidic device also includes a temperature modulation assembly 114 arranged proximate to the cartridge assembly, which temperature modulation assembly comprises at least one heat source that selectively thermally communicates with one or more of the plurality of wells and/or the channel of the magnetofluidic cartridge, for example, to selectively melt temperature sensitive materials disposed between wells.

Figure 3A:
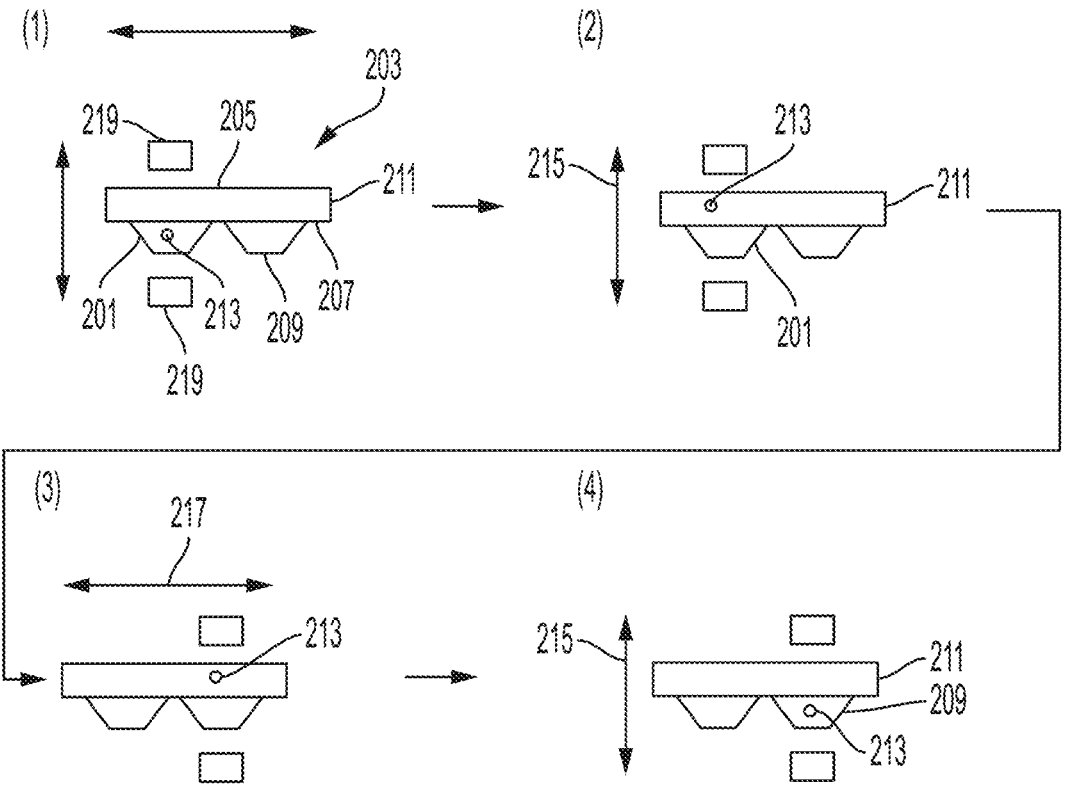
FIG. 3A is schematically shows the use of a magnetofluidic device according to one exemplary embodiment.

FIG. 3A is a schematic showing an exemplary method of detecting a nucleic acid sequence of a nucleic acid molecule in a sample, including the steps of: loading the sample into a sample well 201 of a magnetofluidic cartridge 203 so as to contact the nucleic acid molecule with a magnetic particle 213 such that the nucleic acid molecule binds to the magnetic particle 213 and melting temperature sensitive material (not shown) (step 1); manipulating the magnetic particle 213 bound to the nucleic acid molecule along a first degree of freedom 215 so as to be able to draw the magnetic particle bound to the nucleic acid molecule out of the sample well 201 and into a spacer layer 211 of the magnetofluidic cartridge (step 2); manipulating the magnetic particle 213 bound to the nucleic acid molecule along a second degree of freedom 217 so as to be able translocate the magnetic particle bound to the nucleic acid molecule within the spacer layer to a position above a detection well of the magnetofluidic cartridge (step 3); manipulating the magnetic particle 213 bound to the nucleic acid molecule along the first degree of freedom 215 so as to be able to draw the magnetic particle bound to the nucleic acid molecule out of spacer layer 211 and into the detection well 209 (step 4). The method also includes heating the nucleic acid molecule such that amplification of the nucleic acid sequence occurs; and detecting the nucleic acid sequence. In such an embodiment, manipulation of the magnetic particle bound to the nucleic acid along a first degree of freedom and manipulation of the magnetic particle bound to the nucleic acid along a second degree of freedom includes the use of a pair of magnets 219 arranged to be on opposing sides of the magnetofluidic cartridge with the sample well and the detection well therebetween.

Figure 3B:
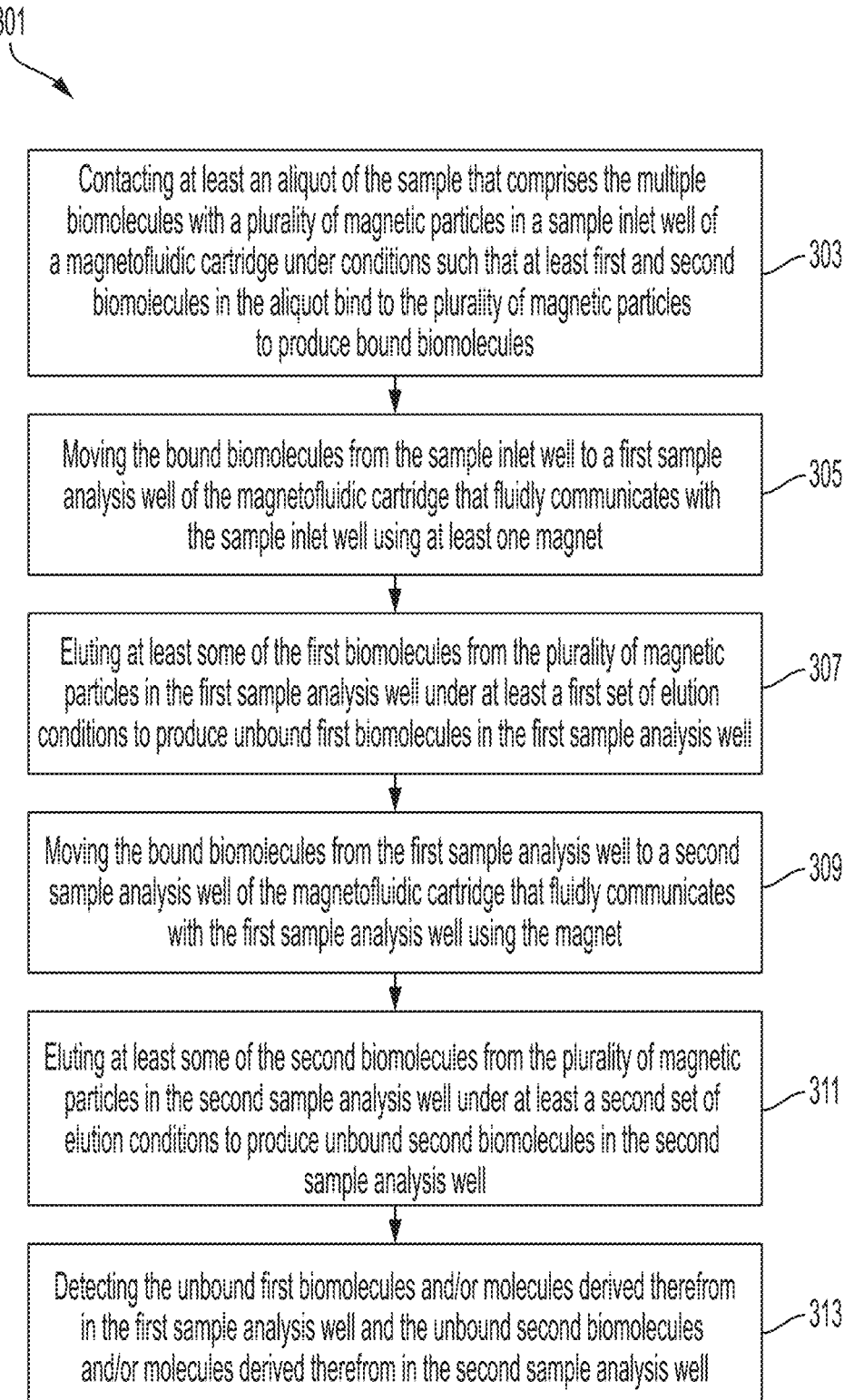
FIG. 3B is a flow chart that schematically shows exemplary method steps of detecting multiple biomolecules in a sample according to some aspects disclosed herein.

FIG. 3B is a flow chart that schematically shows exemplary method steps of detecting multiple biomolecules in a sample according to some aspects disclosed herein. As shown, method 301 includes contacting at least an aliquot of the sample that comprises the multiple biomolecules with a plurality of magnetic particles in a sample inlet well of a magnetofluidic cartridge under conditions such that at least first and second biomolecules in the aliquot bind to the plurality of magnetic particles to produce bound biomolecules (step 303) and moving the bound biomolecules from the sample inlet well to a first sample analysis well of the magnetofluidic cartridge that fluidly communicates with the sample inlet well using at least one magnet (step 305). Method 301 also includes eluting at least some of the first biomolecules from the plurality of magnetic particles in the first sample analysis well under at least a first set of elution conditions to produce unbound first biomolecules in the first sample analysis well (step 307) and moving the bound biomolecules from the first sample analysis well to a second sample analysis well of the magnetofluidic cartridge that fluidly communicates with the first sample analysis well using the magnet (step 309). Additionally, method 301 also includes eluting at least some of the second biomolecules from the plurality of magnetic particles in the second sample analysis well under at least a second set of elution conditions to produce unbound second biomolecules in the second sample analysis well (step 311) and detecting the unbound first biomolecules and/or molecules derived therefrom in the first sample analysis well and the unbound second biomolecules and/or molecules derived therefrom in the second sample analysis well, thereby detecting the multiple biomolecules in the sample (step 313).

An embodiment of the present disclosure relates to a magnetofluidic device for assaying a nucleic acid or other biomolecule from a sample, the device having: a cartridge assembly structured to accept and secure a magnetofluidic cartridge to be used for the assaying; and a magnetic particle manipulation assembly arranged proximate the cartridge assembly, the magnetic particle manipulation assembly having a pair of magnets arranged to be on opposing sides of the magnetofluidic cartridge and which are substantially aligned along a line that will be transverse to the magnetofluidic cartridge such that the line can be aligned with a well in the magnetofluidic cartridge. The pair of magnets are at least one of moveable along the line relative to the magnetofluidic cartridge, or a strength of the pair of magnets is adjustable such that a plurality of magnetic particles when contained within the well can be drawn out of and back into the well during operation.

An embodiment of the present disclosure relates to the magnetofluidic device as described herein, where the magnetic particle manipulation assembly is further structured to provide manipulation of the plurality of magnetic particles, after being drawn out of the well, along a second degree of freedom so as to be able to move the plurality of magnetic particles from the well to a second well in the magnetofluidic cartridge.

An embodiment of the present disclosure relates to the magnetofluidic device as described herein, further having a temperature control assembly arranged proximate the cartridge assembly, the temperature control assembly having a heat exchange portion structured and arranged to be in thermal connection with at least one well in the magnetofluidic cartridge.

An embodiment of the present disclosure relates to the magnetofluidic device as described herein, where the heat exchange portion is a heat block that has a shape that is at least partially complementary to a shape of the at least one well to provide an enhanced surface for heat exchange therethrough, and where the temperature control assembly further includes: a heater in thermal contact with the heat block; a temperature sensor in thermal contact with the heat block; a cooling system in thermal contact with the heat block; and a temperature control device configured to receive temperature signals from the temperature sensor and to provide control signals to the heater and the cooling system.

An embodiment of the present disclosure relates to the magnetofluidic device as described herein, where the magnetic particle manipulation assembly further includes: a first actuator assembly operatively connected to the pair of magnets such that the pair of magnets can be moved in unison, back and forth along the line, and a second actuator assembly operatively connected to the pair of permanent magnets such that the pair of permanent magnets can be moved in unison from a location of the well to a location of a second well. The pair of magnets is a pair of permanent magnets.

An embodiment of the present disclosure relates to the magnetofluidic device as described herein, where the second actuator assembly is a rotational assembly, the second degree of freedom being a rotational degree of freedom. An embodiment of the present disclosure relates to the magnetofluidic device as described herein, where the pair of magnets is a pair of electromagnets configured to provide an electronically adjustable magnetic field therebetween. An embodiment of the present disclosure relates to the magnetofluidic device as described herein, further including a detection system arranged proximate the cartridge assembly so as to be able to detect a physical parameter for a test concerning the biomolecules.

An embodiment of the present disclosure relates to the magnetofluidic device as described herein, further including a temperature control assembly arranged proximate the cartridge assembly, the temperature control assembly having a heat exchange portion structured and arranged to be in thermal connection with at least one well in the magnetofluidic cartridge. An embodiment of the present disclosure relates to the magnetofluidic device as described herein, where the detection system includes: an optical source arranged to illuminate a sample well to excite fluorescent molecules therein, and an optical detector arranged to detect fluorescence emissions from the sample well. An embodiment of the present disclosure relates to the magnetofluidic device as described herein, where the detection system includes a confocal epifluorescence detector. An embodiment of the present disclosure relates to the magnetofluidic device as described herein, where the magnetofluidic device is a portable device. An embodiment of the present disclosure relates to the magnetofluidic device as described herein, where the magnetofluidic device is a handheld device.

An embodiment of the present disclosure relates to a magnetofluidic cartridge for assaying a nucleic acid sequence or other biomolecule from a sample, the cartridge including: a top layer; and a bottom layer spaced apart from the top layer in a generally parallel orientation with respect to the top layer, the bottom layer defining a plurality of wells therein that protrude from a surface of the bottom layer. The at least one of the plurality of wells having a wall sufficiently thin to allow a heat transfer rate such that a nucleic acid amplification assay can be completed in under 20 minutes. An embodiment of the present disclosure relates to the magnetofluidic cartridge as described herein, where one of the plurality of wells has a wall of between 0.05-0.5 mm in thickness. An embodiment of the present disclosure relates to the magnetofluidic cartridge as described herein, further including a spacer layer between and in contact with the top and bottom layers at least along a periphery thereof to seal contents within the magnetofluidic cartridge.

An embodiment of the present disclosure relates to the magnetofluidic cartridge above, where further including a plurality of magnetic particles preloaded into at least one of the plurality of wells, where the at least one of the plurality of wells is a sample well having a port for disposing a sample therein during use, and where the plurality of magnetic particles are coated magnetic nanoparticles that are coated so as to adhere to nucleic acids or other biomolecules via electrostatic or intermolecular forces. An embodiment of the present disclosure relates to the magnetofluidic cartridge above, further having: a plurality of processing fluids each preloaded in a respective one of the plurality of wells; and a sealing fluid preloaded into the magnetofluidic cartridge between the top and bottom layers. The sealing fluid is immiscible with the plurality of processing fluids so as to provide containment of each of the plurality of processing fluids in a respective one of the plurality of wells, and the sealing fluid is hydrophobic.

An embodiment of the present disclosure relates to the magnetofluidic cartridge as described herein, where each of the plurality of processing fluids preloaded into the magnetofluidic cartridge are selected in number and type according to the test to be performed. An embodiment of the present disclosure relates to the magnetofluidic cartridge as described herein, where at least one of the plurality of processing fluids includes a reagent for a nucleic acid amplification assay. An embodiment of the present disclosure relates to the magnetofluidic cartridge as described herein, where the magnetofluidic cartridge is self-contained and remains sealed other than to receive a sample during an entirety of the nucleic acid amplification assay.

An embodiment of the present disclosure relates to a method of detecting a biomolecule in a sample, including: loading the sample into a sample well of a magnetofluidic cartridge so as to contact the biomolecule with a magnetic particle such that the biomolecule binds to the magnetic particle; manipulating the magnetic particle bound to the biomolecule along a first degree of freedom so as to be able to draw the magnetic particle bound to the biomolecule out of the sample well and into a spacer layer of said magnetofluidic cartridge; manipulating the magnetic particle bound to the biomolecule along a second degree of freedom so as to be able translocate the magnetic particle bound to the biomolecule within the spacer layer to a position above a detection well of the magnetofluidic cartridge; manipulating the magnetic particle bound to the biomolecule along the first degree of freedom so as to be able to draw the magnetic particle bound to the biomolecule out of spacer layer and into the detection well; heating the biomolecule such that amplification of the biomolecule occurs; and detecting the biomolecule.

An embodiment of the present disclosure relates to a method as described herein, where the manipulating the magnetic particle bound to the biomolecule along a first degree of freedom and the manipulating the magnetic particle bound to the biomolecule along a second degree of freedom includes the use of a pair of magnets arranged to be on opposing sides of said magnetofluidic cartridge with the sample well and said detection well therebetween. An embodiment of the present disclosure relates to the method as described herein, where amplifying the biomolecule includes the use of a temperature control assembly arranged proximate the cartridge assembly and being structured to receive the detection well in a heat exchange portion of the temperature control assembly. An embodiment of the present disclosure relates to the method as described herein, where heating the biomolecule includes heating the biomolecule such that amplification of the biomolecule occurs in under 20 minutes.

An embodiment of the present disclosure relates to a method of detecting a nucleic acid sequence of a nucleic acid molecule in a sample, including: loading the sample into a sample well of a magnetofluidic cartridge so as to contact the nucleic acid molecule with a magnetic particle such that the nucleic acid molecule binds to the magnetic particle; manipulating the magnetic particle bound to the nucleic acid molecule along a first degree of freedom so as to be able to draw the magnetic particle bound to the nucleic acid molecule out of the sample well and into a spacer layer of the magnetofluidic cartridge; manipulating the magnetic particle bound to the nucleic acid molecule along a second degree of freedom so as to be able translocate the magnetic particle bound to the nucleic acid molecule within the spacer layer to a position above a detection well of the magnetofluidic cartridge; manipulating the magnetic particle bound to the nucleic acid molecule along the first degree of freedom so as to be able to draw the magnetic particle bound to the nucleic acid molecule out of spacer layer and into the detection well; heating the nucleic acid molecule such that amplification of the nucleic acid sequence occurs; and detecting the nucleic acid sequence.

An embodiment of the present disclosure relates to the method of detecting a nucleic acid sequence of a nucleic acid molecule in a sample as described herein, where the manipulating the magnetic particle bound to the nucleic acid molecule along a first degree of freedom and the manipulating the magnetic particle bound to the nucleic acid molecule along a second degree of freedom includes the use of a pair of magnets arranged to be on opposing sides of the magnetofluidic cartridge with the sample well and the detection well therebetween. An embodiment of the present disclosure relates to the method of detecting a nucleic acid sequence of a nucleic acid molecule in a sample as described herein, where the amplifying the nucleic acid sequence includes the use of a temperature control assembly arranged proximate the cartridge assembly and being structured to receive the detection well in a heat exchange portion of the temperature control assembly. An embodiment of the present disclosure relates to the method of detecting a nucleic acid sequence of a nucleic acid molecule in a sample as described herein, where the heating the nucleic acid includes heating the nucleic acid such that amplification of the nucleic acid occurs in under 20 minutes.

An embodiment of the present disclosure relates to a method of assembling a magnetofluidic cartridge including: forming a first layer defining a plurality of wells therein that protrude from a surface of the bottom layer; forming a second layer defining an inlet for injection of a sample into one of the plurality of wells; and sealing the first layer to the second layer such that the first layer and the second layer are configured to reserve a space located between the first layer and the second layer. Forming the first layer includes heating and molding a first film, forming the second layer includes laser cutting a second film. At least one of the plurality of wells includes a wall sufficiently thin to allow a heat transfer rate such that a nucleic acid amplification assay can be completed in under 20 minutes.

An embodiment of the present disclosure relates to the method of assembling a magnetofluidic cartridge as described herein, further including loading a plurality of magnetic particles into at least one of the plurality of wells prior to sealing the first layer to the second layer. An embodiment of the present disclosure relates to the method of assembling a magnetofluidic cartridge as described herein, further including loading at least one fluid into each of the plurality of wells prior to sealing the first layer to the second layer. An embodiment of the present disclosure relates to the method of assembling a magnetofluidic cartridge as described herein, further including loading a sealing fluid between the first layer and the second layer prior to sealing the first layer to the second layer.

An embodiment of the present disclosure relates to the method of assembling a magnetofluidic cartridge as described herein, where the first layer includes polymethylmethacrylate (PMMA), polypropylene (PP), polyethylene terephthalate (PET), polyethylene terephthalate glycol (PETG), high density polyethylene (HDPE), polytetrafluoroethylene (PTFE), and/or polycarbonate (PC). An embodiment of the present disclosure relates to the method of assembling a magnetofluidic cartridge as described herein, where the second layer includes polymethylmethacrylate (PMMA), polypropylene (PP), polyethylene terephthalate (PET), polyethylene terephthalate glycol (PETG), high density polyethylene (HDPE), polytetrafluoroethylene (PTFE), and/or polycarbonate (PC).

An embodiment of the present disclosure relates to the method of assembling a magnetofluidic cartridge as described herein, where the first layer is between 1.00-8.00 mm in thickness. An embodiment of the present disclosure relates to the method of assembling a magnetofluidic cartridge as described herein, where the second layer is between 0.05-3 mm in thickness. An embodiment of the present disclosure relates to the method of assembling a magnetofluidic cartridge as described herein, where the sealing fluid includes oil, air and wax. An embodiment of the present disclosure relates to the method of assembling a magnetofluidic cartridge as described herein, further including passivating a surface of the plurality of wells prior to sealing the first layer to the second layer.

Some embodiments of the present disclosure are directed to a method for the design and fabrication of a consumable device for use in magnetic particle-driven biochemical assays. Some embodiments of the present disclosure can improve substantially on previously disclosed technology (U.S. Pat. No. 9,463,461) by enabling biochemical processes which require thermal control, e.g. Polymerase Chain Reaction (PCR) or High Resolution Melting Analysis (HRMA).

Some aspects of the present disclosure can include, but are not limited to, the following features:

A device comprising 1) a planar hydrophobic substrate for particle transport and 2) a substrate with one or more extruded space for retention and isolation of one or more biochemical reagents; where the said extruded space includes a thin- walled feature (<0.75 mm in thickness) in relation to the exterior of the device; where the biochemical reagents isolated within the confines of the said extruded space, sharing an interface with a common phase (e.g. air, oil); where the common phase is in contact with each reagents as well as a planar hydrophobic substrate.

A method of particle transport, where one or more magnetic particles are manipulated in two dimensions. The first dimension is defined by the extent of transverse motion of magnetic particles between the innermost part of the extruded feature and the planar hydrophobic substrate. The second dimension is defined by the extent of longitudinal motion of magnetic particles along the planar hydrophobic substrate. Particle extraction, translocation and re-suspension facilitated by magnetic actuation in a combination of the two dimensions, where a two-axis mechanical manipulator is an embodiment.

A method of modulating temperature contained within one or more extruded features to facilitate a biochemical process. An example of such a biochemical process may include but is not limited to PCR, Loop Mediated Isothermal Amplification (LAMP), Helicase Dependent Assay (HAD), Rolling Circle Amplification Assay (RCA), Recombinase Polymerase Amplification (RPA), Reverse-Transcription Polymerase Chain reaction (RT-PCR), Specific High-Sensitivity Enzymatic Reporter UnLOCKing (SHERLOCK), DNA endonuclease-targeted CRISPR trans reporter (DE-TECTR), bacterial culture and HRMA. An example of temperature modulation may include but is not limited to contact heating, radiative heating and photothermal heating.

FIGS. 2A-C and 3 provide schematic illustrations of devices and methods of using the devices according to some embodiments of the present disclosure. A magnetofluidic device for testing biological samples according to an embodiment of the present disclosure includes a cartridge assembly structured to accept and secure a magnetofluidic cartridge to be processed, the magnetofluidic cartridge has a plurality of wells including at least a sample well and a detection well each of which protrudes beyond a surface of the magnetofluidic cartridge; and a magnetic particle manipulation assembly arranged proximate the cartridge assembly, the magnetic particle manipulation assembly being structured to provide manipulation of magnetic particles contained within the magnetofluidic cartridge along a first degree of freedom so as to be able to draw magnetic particles into and out of each of the plurality of wells. The magnetic particle manipulation assembly is further structured to provide manipulation of magnetic particles contained within the magnetofluidic cartridge along a second degree of freedom so as to be able to move magnetic particles from one of the plurality of wells to another one of the plurality of wells.

The magnetofluidic device can further include a detection system arranged proximate the cartridge assembly so as to be able to detect a physical parameter for a test concerning a genetic sample. The magnetofluidic device can further include a temperature control assembly arranged proximate the cartridge assembly that is also structured to receive at least the detection well in a heat exchange portion of the temperature control assembly. In some embodiments, the temperature control assembly includes a heat block defining the heat exchange portion therein for receiving the sample well, a heater in thermal contact with the heat block, a temperature sensor in thermal contact with the heat block, a cooling system in thermal contact with the heat block, and a temperature control device configured to receive temperature signals from the temperature sensor and to provide control signals to the heater and the cooling system.

In some embodiments, the magnetic particle manipulation assembly includes a pair of permanent magnets arranged to be on opposing sides of the magnetofluidic cartridge with one of the plurality of wells therebetween, a first actuator assembly operatively connected to the pair of permanent magnets such that the pair of permanent magnets can be moved in unison, back and forth along an axis to move magnetic particles into and out of one of the plurality of wells, and a second actuator assembly operatively connected to the pair of permanent magnets such that the pair of permanent magnets can be moved in unison from a location of one of the plurality of wells therebetween to a location with a second one of the plurality of wells therebetween. In some embodiments, the second actuator assembly is a rotational assembly such that the second degree of freedom is a rotational degree of freedom.

In some embodiments, the detection system includes an optical source arranged to illuminate the sample well to excite fluorescent molecules therein, and an optical detector arranged to detect fluorescence emissions from the sample well. In some embodiments, the detection system is or includes a confocal epifluorescence detector. In some embodiments, the magnetofluidic device is a portable device. In some embodiments, the magnetofluidic device is a handheld device.

In some embodiments, a magnetofluidic cartridge for a magnetofluidic device for testing genetic samples includes a top layer; a bottom layer spaced apart from the top layer in a generally parallel orientation with respect to the top layer; and a spacer layer between and in contact with the top and bottom layers at least along a periphery thereof to seal contents within the magnetofluidic cartridge. The bottom layer defines a plurality of wells therein that protrude from a surface of the bottom layer.

In some embodiments, the magnetofluidic cartridge can further include a plurality of processing fluids or in lyophilized forms each preloaded in a respective one of the plurality of wells; and a sealing fluid preloaded into the magnetofluidic cartridge between the top and bottom layers. The sealing fluid is immiscible with the plurality of processing fluids so as to provide containment of each of the plurality of processing fluids in a respective one of the plurality of wells. In some embodiments, the magnetofluidic cartridge can further include magnetic particles preloaded into at least one of the plurality of wells. This can be a sample well having a port for disposing a sample therein during use. The magnetic particles can be coated magnetic nanoparticles that adhere electrostatically to genetic material. Each of the plurality of processing fluids can be preloaded into the magnetofluidic cartridge and can be selected in number and type according to the test to be performed.

In some embodiments, the magnetofluidic cartridge has a plurality of wells where at least one of the wells has a thin wall to allow for rapid and efficient temperature control during a nucleic acid amplification assay. This allows for the nucleic acid assay to proceed in under 30, 25, 20, 15, 10, or 5 minutes.

In some embodiments, the magnetofluidic device includes a magnetic particle manipulation assembly having a pair of permanent magnets arranged to be on opposing sides of a magnetofluidic cartridge with one of a plurality of wells therebetween. The magnetic particle manipulation assembly has a first actuator assembly operatively connected to the pair of permanent magnets such that the pair of permanent magnets can be moved in unison, back and forth along an axis to move magnetic particles into and out of the one of the plurality of wells, and a second actuator assembly operatively connected to the pair of permanent magnets such that the pair of permanent magnets can be moved in unison from a location of the one of the plurality of wells therebetween to a location with a second one of the plurality of wells therebetween. Such a conformation allows the device to be used with a variety of cartridges having a variety of shaped wells. Also, such a conformation allows for the transport of a magnetic particle bound to a nucleic acid sample from a first aqueous solution in a first well, through a hydrophobic solution, and then into a second aqueous solution in a second well. Such a process allows for the removal of excess solution from the first well prior to entry into the second well.

In some embodiments, the magnetofluidic device is hand held and allows for the extraction of nucleic acids from a sample, the amplification of these nucleic acids, and their subsequent detection on a single platform.

Figure 4:
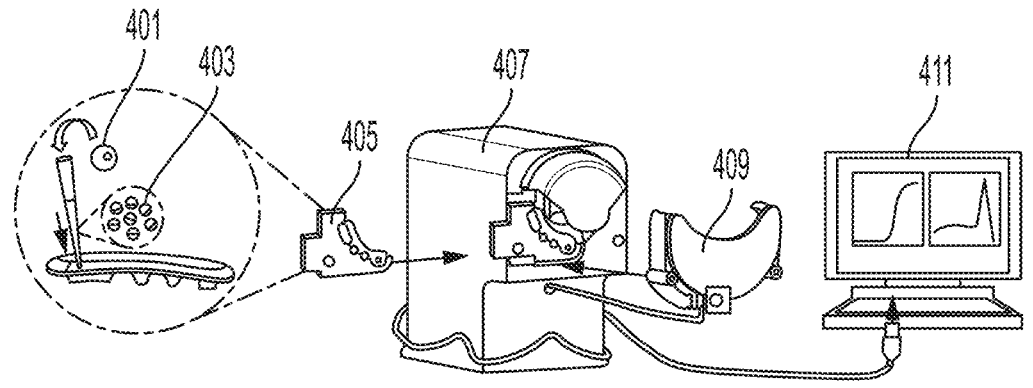
FIG. 4 schematically shows a magnetofluidic device from a perspective view according to one exemplary embodiment.

To further illustrate, FIG. 4 schematically shows a magnetofluidic device from a perspective view according to one exemplary embodiment. As shown, the magnetofluidic device includes housing 407 (e.g., a 3D printed housing) that includes a device as described herein. The device includes cartridge assembly 405 structured to accept and secure a magnetofluidic cartridge as described herein (e.g., into which blood serum 401 and magnetic beads 403 are introduced). The magnetofluidic device also includes PCR thermal control faceplate 409 in this exemplary embodiment. As additionally shown, the magnetofluidic device also communicates (e.g., via a wired or wireless connection) to computer 411 for data analysis.

EXAMPLES

Figure 5:
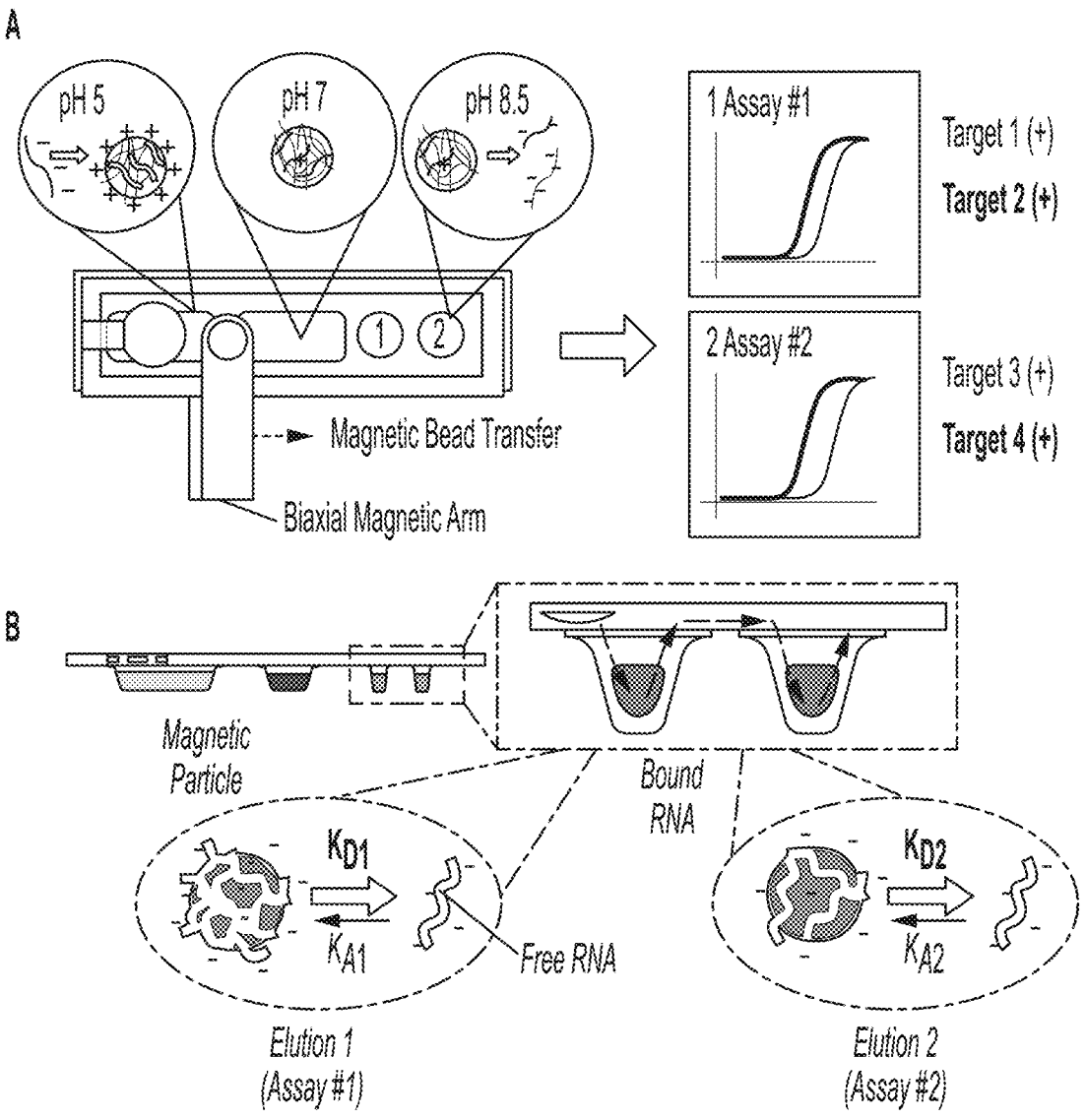
FIG. 5 (panels A and B) schematically depict magnetofluidic assay cartridge operation with sequential elution according to some embodiments. (A) The cartridge operation starts with nucleic acid capture by charge-functionalized magnetic beads in a low pH environment within the first cartridge well. Transport to a neutral pH wash buffer removes assay inhibitors and the nucleic acids are sequentially eluted into two separate assay reagents. In this example, each assay contains PCR with duplexed fluorescent probes for detecting two targets per well. (B) The magnetic beads with bound RNA were first eluted into Assay #1. During the elution of the analytes off the particles, the final elution of nucleic acids was determined by both rate of analytes release into the solution and the rate of the nucleic acids binding to the beads.

Methods
Multiplexed Detection of SARS-CoV-2 with Controls on a Magnetofluidic Cartridge Multiplexed analyte detection of a crude sample using sequential magnetic particle elution was performed in a droplet magnetofluidic cartridge for automated, portable nucleic acid purification and analysis from unprocessed liquid samples. The assay cartridges in this example (FIG. 5A) consist of four wells for (1) sample processing buffer comprising magnetic particles, binding buffer, and control RNA, (2) wash buffer to remove inhibitory compounds, (3) the first assay buffer which produces a signal change when certain specific targets are present (4) a second assay buffer which produces signals for a separate set of targets. A layer of immiscible oil ensures the isolation of aqueous reagents in each well while actuation of opposing magnets transfers the magnetic particles with captured analytes between the wells. The elution of analytes into two sequential assay reagents was controlled to be 1-minute incubation at 55° C. After elution of analytes, the magnetic particles were removed, followed by a 1-minute reverse transcription at 55° C., and 50 cycles with temperature targets of 2 seconds of denaturation at 106° C. followed by 2 seconds of annealing at 50° C. Assay cartridge operation can be found in (FIG. 5A).

Figure 6:
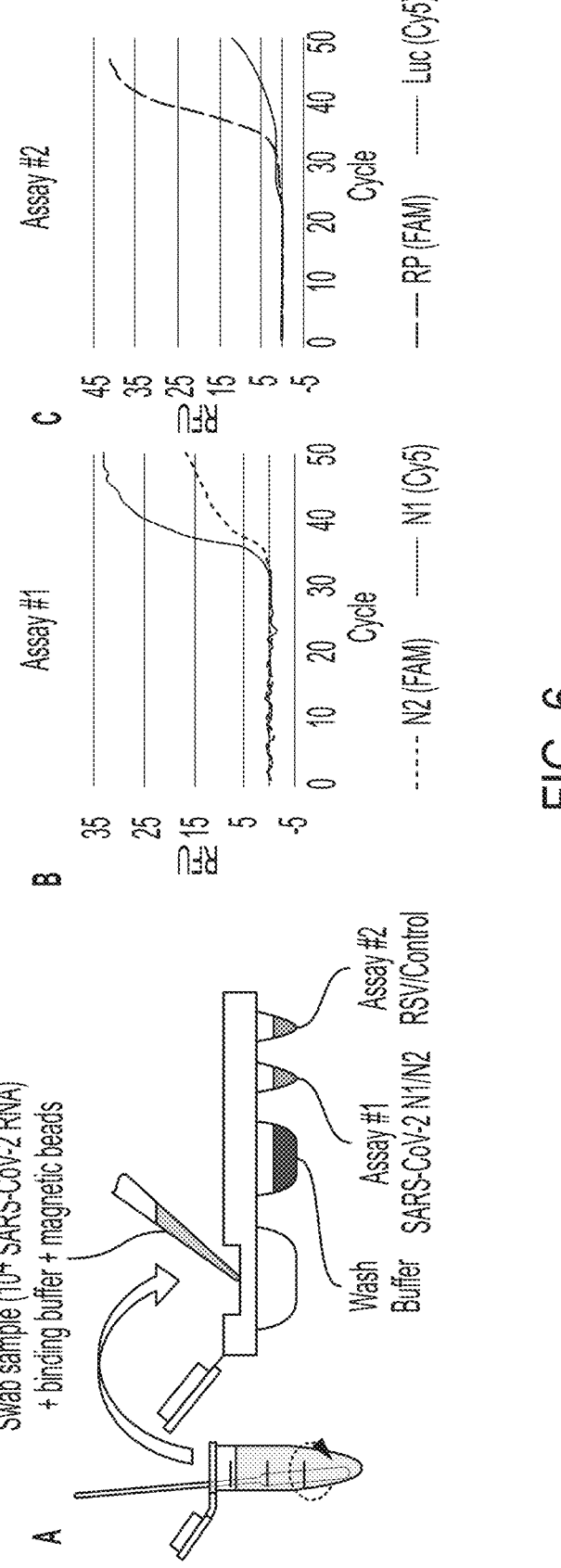
FIG. 6 (panels A-C) schematically illustrate multiplexed detection of SARS-CoV-2 and control assay using a magnetofluidic cartridge according to some embodiments. (A) $10^4$ copies of synthetic SARS-CoV-2 RNA were spiked into a negative swab sample and tested on the cartridge. The third cartridge well consisted of RT-PCR assay (Assay #1) detecting two SARS-CoV-2 targets (N1 and N2) on N gene. The fourth cartridge well consisted of RT-PCR assay (Assay #2) detecting an endogenous control (RNase P gene appearing in human samples), and an internal control RNA (luciferase RNA). (B) After RT-PCR, N1 and N2 were both detected in Assay #1, and (C) RNase P amplification signal and luciferase signal were also both detected in Assay #2.
Figure 7:
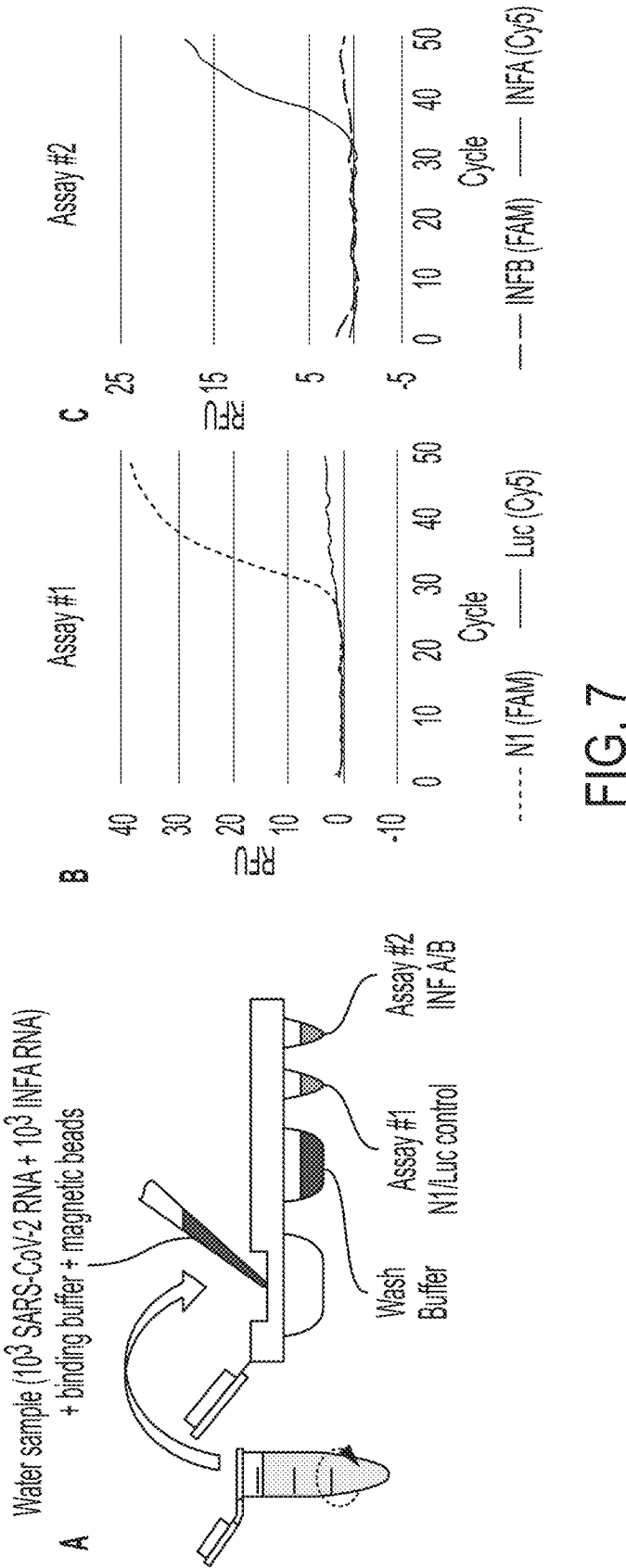
FIG. 7 (panels A-C) schematically illustrate multiplexed detection of multiple infectious agents using magnetofluidic cartridge according to some embodiments. (A) $10^3$ copies of synthetic SARS-CoV-2 RNA and $10^3$ copies Influenza A synthetic RNA were spiked into a water solution and tested on the cartridge. The third cartridge well consisted of RT-PCR assay (Assay #1) detecting one SARS-CoV-2 targets (N1) on N gene and luciferase internal control RNA. The fourth cartridge well consisted of RT-PCR assay (Assay #2) detecting Influenza A and Influenza B target. (B) After RT-PCR, N1 generated a strong amplification signal in Assay #1, and (C) Influenza A signal was positive in Assay #2.
Figure 8:
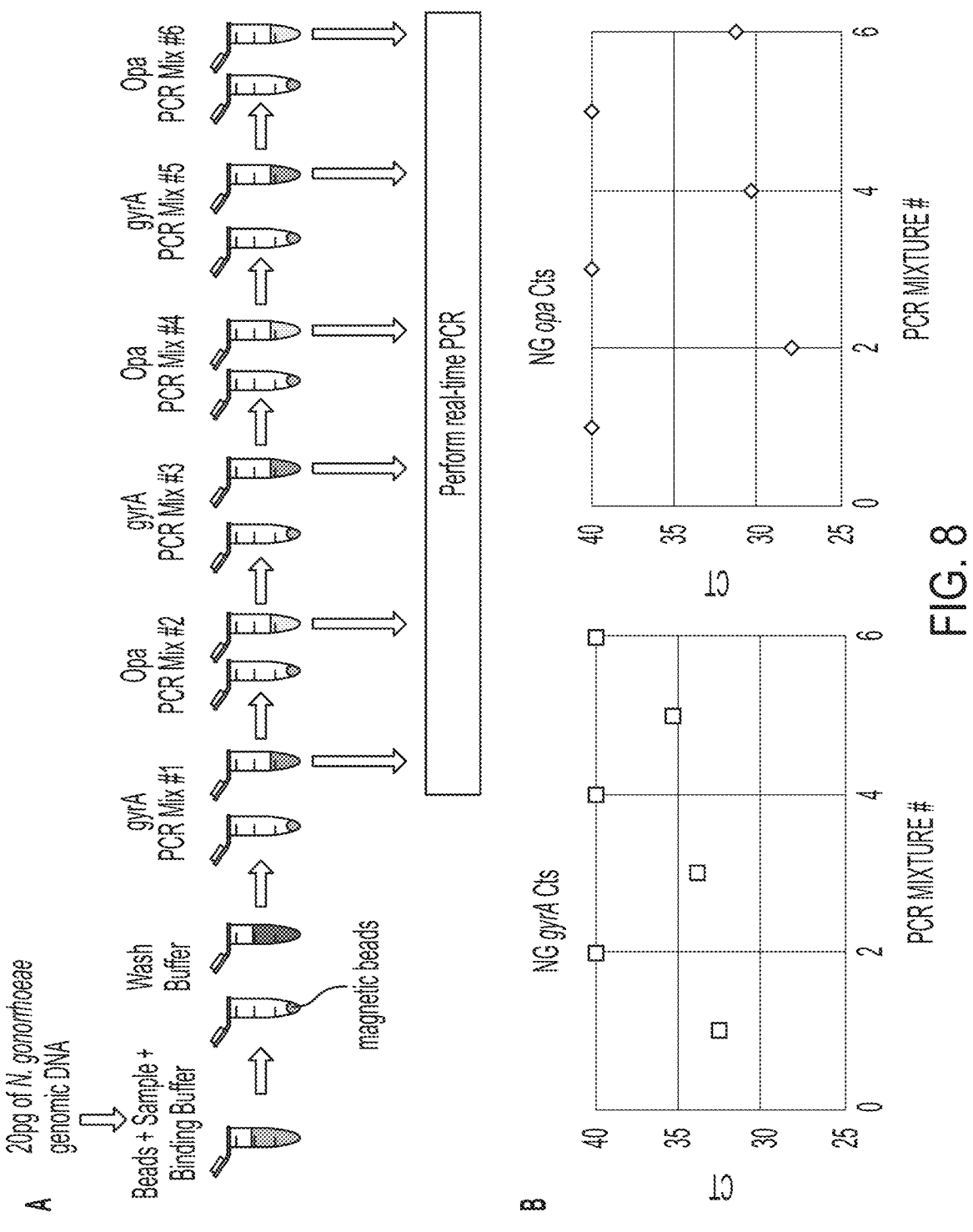
FIG. 8 (panels A and B) schematically show sequential elution of analytes from a single DNA input up to six real-time PCR assays according to some embodiments. (A) A sample containing 20 pg NG genomic DNA was concentrated and transported by the magnetic beads, followed by sequential elution of analytes into six PCR mixture. (B) Cts of six PCR mixture showed that sufficient gDNA were eluted into all of these PCR mixtures, while no crosstalk fluorescent signal between each PCR reaction. Ct equal to 40 was used to represent no amplification at that specific fluorescent channel.

A magnetofluidic cartridge was assembled as outlined in (FIG. 6A). A mixture of 4 μL 25 mg/mL magnetic beads functionalized with pH-responsive electronegative charged species (ChargeSwitch, Invitrogen) were mixed with 20 μL 1M MES buffer, 1 μL of 10% Tween-20 and 1 μL of $10^4$ copies/μL internal control RNA (Luciferase Control RNA, Promega) were prepared. The beads mixture was mixed with an 80 μL negative nasopharyngeal swab eluate spiked with $10^4$ SARS-CoV-2 synthetic RNA and spiked into the first cartridge well. Robotic actuation of permanent magnets transferred the magnetic beads through 50 μL wash buffer in the second cartridge well followed by elution into the third well containing 7.5 μL of reverse-transcription polymerase chain reaction (RT-PCR) buffer amplifying two sequences of the SARS-CoV-2 N gene (N1, N2) with fluorescent signals generated with duplexed hydrolysis probes. After the elution into the first RT-PCR buffer, the beads were transferred into the fourth cartridge well containing another 7.5 μL RT-PCR mix amplifying the internal control (luciferase RNA preloaded with the beads) and the RNase P gene endogenous to the human sample. Finally, the cartridge assay wells underwent thermocycling with fluorescence detection.
Multiplexed Detection of Multiple Infectious Agents from a Single Specimen A cartridge similar to the one described above was assembled with the third cartridge well containing RT-PCR reagents for amplifying the SARS-CoV-2 N1 target and luciferase internal control, while the fourth cartridge well contained RT-PCR reagents for amplifying separate Influenza A and Influenza B sequences (FIG. 7). The sample consisting of 100 μL water spiked with $10^3$ copies SARS-CoV-2 synthetic RNA and $10^3$ copies Influenza A synthetic RNA (ATCC® VR-95DQ™) was mixed with 4 μL magnetic beads, 20 μL 1M MES, 1 μL of 10% Tween-20 and 1 μL of $10^4$ copies/μL luciferase RNA (7A). The sample mixture was spiked in the first cartridge well for automated sample processing and RT-PCR.
Sequential Elution of Analytes into a Series of Assay Reagents from a Single Specimen Input A 10 μL aqueous solution containing $10^4$ copies extracted N. gonorrhoeae (NG) genomic DNA (ATCC 49226) was combined with 30 μL binding buffer B12 (ChargeSwitch, Invitrogen) and 4 μL 25 mg/mL magnetic beads were added into the DNA solution and were fully mixed. After a 1-minute incubation, magnetic beads were attracted by a magnet and were moved out of the liquid phase, followed by the sample mixture being aspirated. The magnetic beads were then exposed to a neutral pH wash buffer to remove inhibitory compounds, followed by magnetic removal of the beads and aspiration of the wash buffer. Magnetic beads were added to a 10 μL PCR solution for 1-minute incubation at room temperature, followed by magnetic extraction and aspiration of the PCR solution. The elution process was repeated for 6 times, in which the 1st, 3rd, and 5th elution used PCR assay reagents targeting the gyrA gene, 2nd, 4th and 6th elution used PCR assay targeting the opa gene. The entire process is depicted in (FIG. 8A). After the multi-elution process, the PCR solutions used for elution were run for 40 cycles of real-time PCR.
Temperature-Mediated Elution Control To demonstrate temperature control over the proportion of analytes eluted in each elution, 4 μL magnetic beads were bound with $10^4$ copies SARS-CoV-2 synthetic RNA (ATCC® VR-3276SD™) and washed with the same processes mentioned above. The magnetic particles were then transferred into 10 μL SARS-CoV-2 N1 RT-PCR and incubated at 20, 40, 50, 60 or 70° C. to elute the bound RNA.

Figure 9:
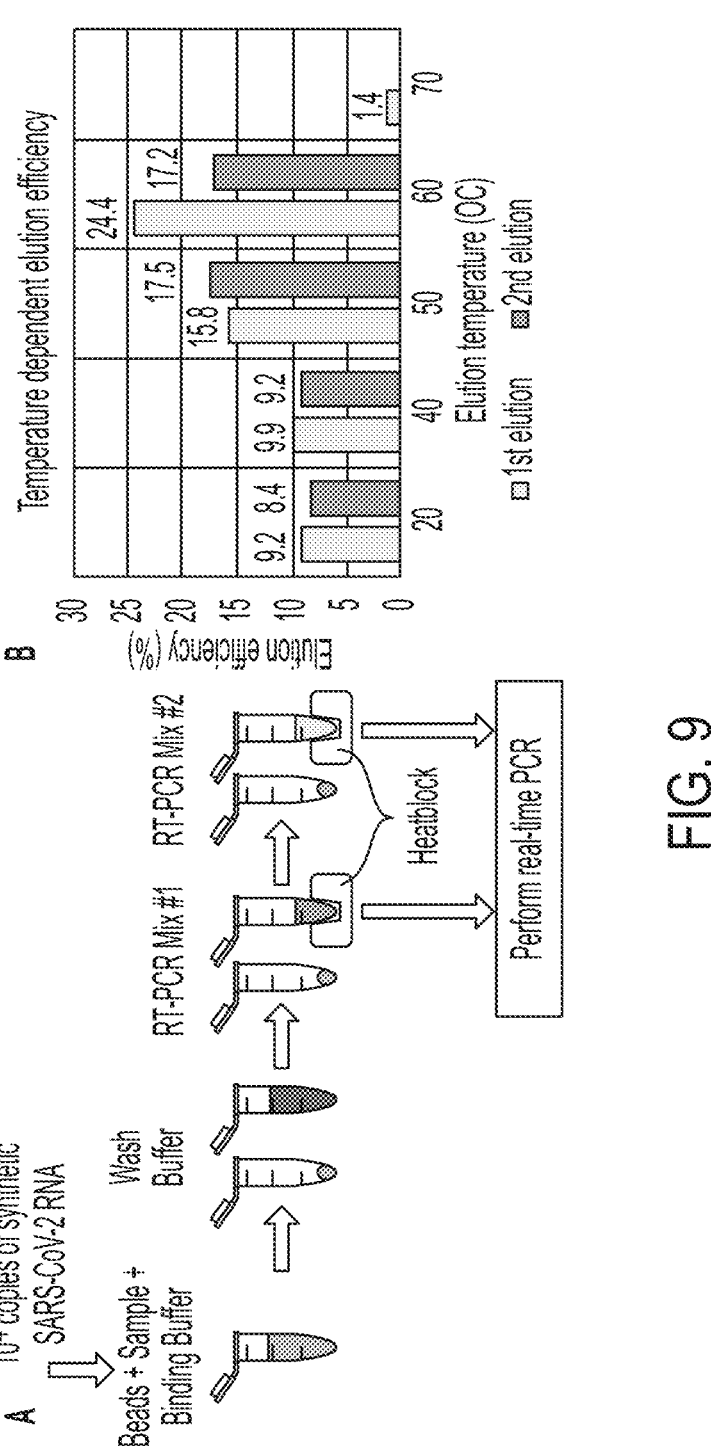
FIG. 9 (panels A and B) schematically depict temperature-mediated elution control according to some embodiments. (A) $10^4$ copies of synthetic SARS-CoV-2 RNA were concentrated by the magnetic beads and eluted sequentially into two separate RT-PCR mixtures (#1 and #2). In each group, the elution was performed at a specific temperature for 1 minute. (B) Elution efficiency was calculated as 100 * detected copies number (calculated based on standard curve in the same PCR plate) divided by $10^4$ copies. With a higher elution temperature, the elution efficiency was higher for eluting in both RT-PCR mixture #1 and RT-PCR mixture #2.

After elution, magnetic particles were removed and the solutions were subjected to 40 cycles of RT-PCR. The entire process is depicted in (FIG. 9A).

Time-Mediated Elution Control

To demonstrate how elution time affects the proportion of analytes released, 4 μL magnetic particles bound with $10^4$ copies of synthetic SARS-CoV-2 RNA were washed and eluted consecutively into two 10 μL RT-PCR buffer targeting the N1 gene with each elution step incubated at 50° C. for 30 seconds, 60 seconds, 90 seconds or 120 seconds (FIG. 10A).

Tunable Elution Efficiency Using Multi-Elution Scheme

In this example, magnetic particles bound with $10^4$ copies SARS-CoV-2 synthetic RNA were washed and subjected to sequential elution in RT-PCR buffers with the following conditions prior to thermocycling: (1) 1st elution at 50° C. for 10 seconds, 2nd elution at 60° C. for 2 minutes, (2) 1st elution at 60° C. for 2 minutes, 2nd elution at 50° C. 10 seconds, (3) 1st elution at 50° C. for 10 seconds, 2nd elution at 50° C. for 10 seconds, (4) 1st elution at 60° C. for 2 minutes, 2nd elution at 60° C. for 2 minutes, and (5) 1st elution at 50° C. 1 minute, 2nd elution at 50° C. 1 minute.

Multi-Elution Scheme on an Automated Liquid Handler

Figure 12:
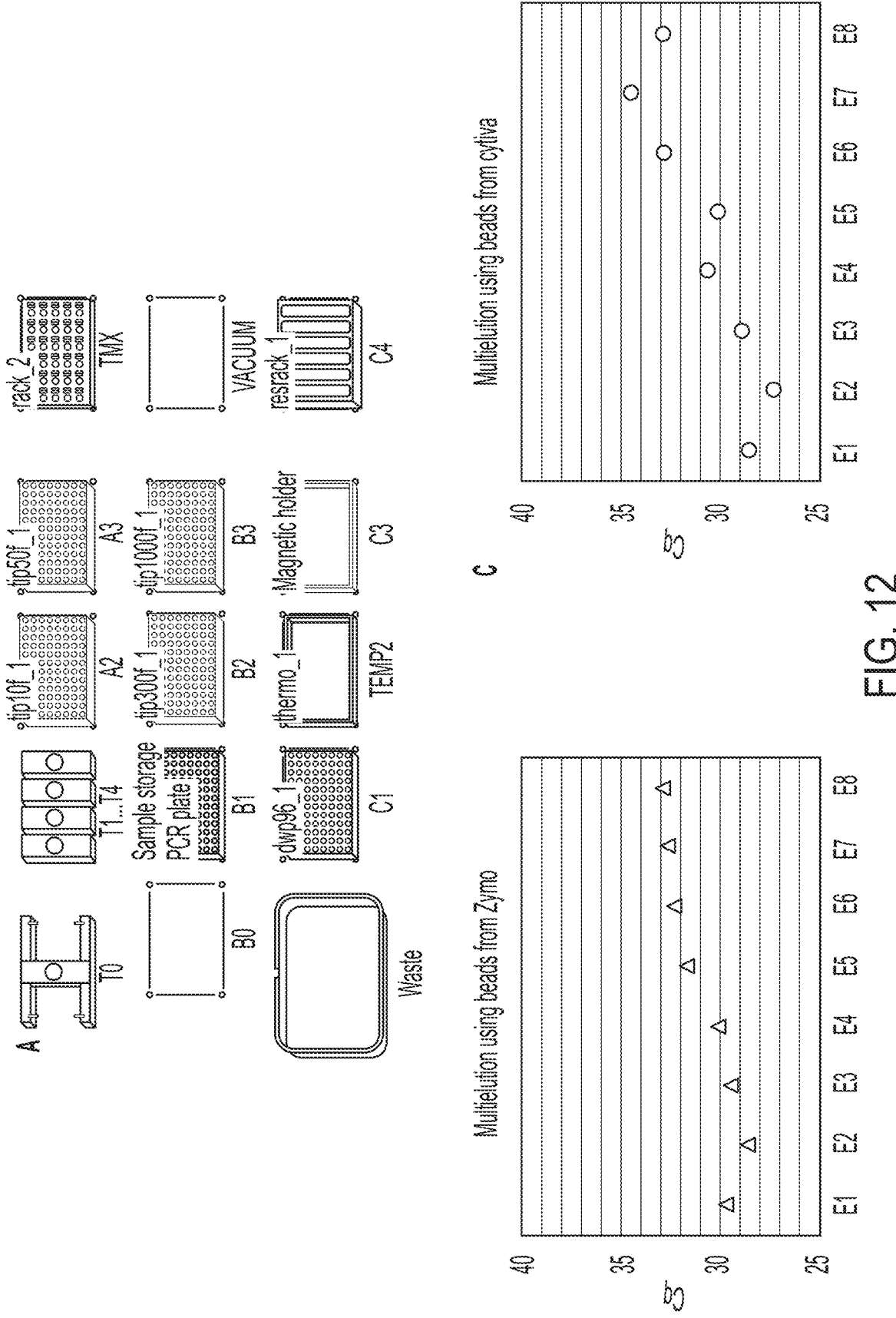
FIG. 12 (panels A-C) schematically depicts a multi-elution scheme on an automated pipetting. Two individual samples containing 100 pg of extracted C. trachomatis (CT) genomic DNA were concentrated by the magnetic beads from (A) Zymo research and (B) from Cytiva. Beads concentrated the DNA and were washed with wash buffer, followed by eluted sequentially into eight separate elution buffers. The entire process was automated by the custom script that ran on Eppendorf epMotion 5075 Liquid Handler.

Sequential magnetic particle elution to concentration nucleic acid from a single specimen input and elute nucleic acid to 8 multiple assay reagents was programmed to be fully automated on a commercially available automated pipetting system (Eppendorf epMotion 5075 Liquid Handler, Eppendorf). Extracted genomic DNA from *C. trachomatis* (CT) were prepared at the concentration of 1 pg per microliter. Binding buffer (4M GuSCN in 55 mM Tris HCl pH 7.5+25 mM EDTA), wash buffer (20% PEG+Tween-20) was enough to process at least 4 samples. Two different sources of magnetic beads (MagBinding Beads from Zymo Research and SeraSil-Mag™ 400 beads from Cytiva) were used in this test. Elution buffer was enough for at least 40 eluates. A representation of the worktable setup is shown in FIG. 12A. Table 1 show the required reagents and the reagent positions within the reagent rack. Table 2 shows the description of the automated method commands. After the multi-elution process, the 8 eluates for each sample were run for 40 cycles of real-time PCR.

TABLE 1

| epMotion 5075 worktable details for automated multielution | |
| --- | --- |
| Position | Tools or Disposables |
| T0 | Gripper |
| T1 | Pipette |
| A2 | Tip 10 |
| A3 | Tip 50 |
| TMX | Binding Buffer |
| | Cytiva Beads |
| | CT DNA target |
| | PEG Wash Buffer |
| | PCR Mastermix |
| | Initial Target |
| | DEPC H2O |
| | Zymo Beads |
| B1 | Empty 96 well plate |
| B2 | Tip 300 |
| B3 | Tip 1000 |
| C1 | 96-Well DeepWell ™ |
| C3 | Magnetic holder |
| C4 | Empty tube |
| | Elution Buffer |

TABLE 2

| epMotion programm description for automated multielution | | |
| --- | --- | --- |
| Step | Command | Purpose |
| 1 | Number of samples | Setup CT DNA sample into 4 tubes of deep well plate |
| 2 | Reagent transfer | Dispense binding buffer |
| 3 | Reagent transfer | Dispense beads from Zymo in first 2 DNA samples |
| 4 | Reagent transfer | Dispense beads from cytiva in the next 2 DNA samples |
| 5 | Wait | 5 min |
| 6 | Transport | Transfer deep well plate to magnetic holder |
| 7 | Reagent transfer | Pellet beads and remove buffer into waste |
| 8 | Transport | Transfer deep well plate to rest rack |
| 9 | Reagent transfer | Dispense wash buffer |
| 10 | Transport | Transfer deep well plate to magnetic holder |
| 11 | Reagent transfer | Pellet beads and remove buffer into waste |
| 12 | Transport | Transfer deep well plate to rest rack |
| 13 | Reagent transfer | Dispense wash buffer |
| 14 | Transport | Transfer deep well plate to magnetic holder |
| 15 | Reagent transfer | Pellet beads and remove buffer into waste |
| 16 | Transport | Transfer deep well plate to rest rack |
| 17 | Reagent transfer | Dispense elution buffer |
| 18 | Wait | 1 min |
| 19 | Transport | Transfer deep well plate to magnetic holder |
| 20 | Reagent transfer | Pellet beads and remove eluate into 96 well PCR plate |
| 21-55 | | Repeat step 16 to step 20 for 7 times |

PCR Assay Conditions

RT-PCR buffers for synthetic SARS-CoV2 RNA targets (2019-nCoV CDC RUO Plasmid Control, Integrated DNA Technologies) were prepared in 7.5 μL reaction volumes containing 3.75 μL 2× qScript XLT 1-Step RT-qPCR ToughMix (Quantabio), 1 U SpeedSTAR HS DNA polymerase (Takara Bio), 0.75 μM final concentration of N2 forward and N2 reverse primers, 0.25 μM final concentration of FAM-tagged N2 hydrolysis probe, 0.50 μM final concentration of N1 forward and N1 reverse primers, 0.25 μM final concentration of Cy5-tagged N1 hydrolysis probe, 1 mg/mL BSA (NEB), and 0.1% Tween-20 (Sigma-Aldrich).

RT-PCR buffers for luciferase (Luc) RNA internal control and human RNase P (RP) gene were prepared in 7.5 μL reaction volumes containing 3.75 μL 2× qScript XLT 1-Step RT-qPCR ToughMix (Quantabio), 1 U SpeedSTAR HS DNA polymerase (Takara Bio), 0.5 μM final concentration of Luc forward and Luc reverse primers, 0.25 μM final concentration of TYE-tagged Luc hydrolysis probe, 0.50 μM final concentration of RP forward and RP reverse primers, 0.25 μM final concentration of FAM-tagged RP hydrolysis probe, 1 mg/mL BSA, and 0.1% Tween-20.

RT-PCR buffers for synthetic INF A targets (ATCC® VR-95DQ™) and synthetic INF B RNA (ATCC® VR-1535D) were prepared in 7.5 μL reaction volumes containing 3.75 μL 2× qScript XLT 1-Step RT-qPCR ToughMix (Quantabio), 1 U SpeedSTAR HS DNA polymerase (Takara Bio), 0.5 μM final concentration of INF A forward and INF A reverse primers, 0.25 μM final concentration of TYE-tagged INF A hydrolysis probe, 0.50 μM final concentration of INF B forward and INF B reverse primers, 0.25 μM final concentration of FAM-tagged INFB hydrolysis probe, 1 mg/mL BSA, and 0.1% Tween-20.

RT-PCR buffers for synthetic SARS-CoV-2 N1 target were prepared in 7.5 μL reaction volumes containing 3.75 μL 2× qScript XLT 1-Step RT-qPCR ToughMix (Quantabio), 0.5 μM final concentration of INF A forward and INF A reverse primers, 0.25 μM final concentration of TYE-tagged hydrolysis probe, 0.50 μM final concentration of INF B forward and INF B reverse primers and 0.25 μM final concentration of FAM-tagged hydrolysis probe.

PCR buffers for NG opa or gyrA genes were prepared in 10 μL reaction volumes containing 1 μL 10× Fast buffer, 0.3 μM forward primer, 0.3 μM reverse primer, 0.2 μM hydrolysis probe, 0.2 μL 10 mM dNTP mix, and 0.25 U Speed-STAR HS DNA polymerase (Takara Bio).

PCR buffer for CT DNA was prepared in 10 μL reaction volumes containing 1 μL 10× Fast buffer, 0.25 μM forward primer, 0.25 μM reverse primer, 0.25 μM hydrolysis probe, 200 nM dNTP mix, and 0.25 U SpeedSTAR HS DNA polymerase (Takara Bio).

All the oligonucleotide sequences were purchased from IDT. Oligo sequences are listed in Table 3.

TABLE 3

Primer sequences in PCR or RT-PCR reactions

| Target | Oligo name | 5' Tag | Sequence | 3' Tag | SEQ ID NO |
|--------|-----------|--------|----------|--------|-----------|
| N1 | Forward primer | | GAC CCC AAA ATC AGC GAA AT | | 1 |
| N1 | Reverse primer | | TCT GGT TAC TGC CAG TTG AAT CTG | | 2 |
| N1 | Probe | TYE665 | ACC CCG CAT TAC GTT TGG TGG ACC | Iowa Black | 3 |
| N2 | Forward primer | | TTA CAA ACA TTG GCC GCA AA | | 4 |
| N2 | Reverse primer | | GCG CGA CAT TCC GAA GAA | | 5 |
| N2 | Probe | FAM | ACA ATT TGC CCC CAG CGC TTC AG | BHQ-1 | 6 |
| INF B | Forward primer | | AAATACGGTGGATTAAACA AAAGCAA | | 7 |
| INF B | Reverse primer | | CCAGCAATAGCTCCGAAGA AA | | 8 |
| INF B | Probe | FAM | CACCCATATTGGGCAATTT CCTATGGC | BHQ-1 | 9 |
| INF A | Forward primer | | CTTCTAACCGAGGTCGAAA CGTA | | 10 |
| INF A | Reverse primer | | GGTGACAGGATTGGTCTTG TCTTTA | | 11 |
| INF A | Probe | TYE665 | TCAGGCCCCCTCAAAGCCG AG | Iowa Black | 12 |
| Luc | Forward primer | | TACAACACCCCAACATCTT CGA | | 13 |
| Luc | Reverse primer | | GGAAGTTCACCGGCGTCAT | | 14 |
| Luc | Probe | TYE665 | CGGGCGTGGCAGGTCTTCC C | Iowa Black | 15 |
| RP | Forward primer | | AGA TTT GGA CCT GCG AGC G | | 16 |
| RP | Reverse primer | | GAG CGG CTG TCT CCA CAA GT | | 17 |
| RP | Probe | FAM | TTC TGA CCT GAA GGC TCT GCG CG | BHQ-1 | 18 |

TABLE 3-continued

Primer sequences in PCR or RT-PCR reactions

| Target | Oligo name | 5' Tag | Sequence | 3' Tag | SEQ ID NO |
|--------|-----------|--------|----------|--------|-----------|
| opa | Forward primer | | TTGAAACACCGCCCGGAA | | 19 |
| opa | Reverse primer | | TTTCGGCTCCTTATTCGGT TTAA | | 20 |
| opa | Probe | Cy5 | CCGATATAATCCGTCCTTC AACATCAG | Iowa Black | 21 |
| gyrA | Forward primer | | TTG CGC CAT ACG GAC GAT | | 22 |
| gyrA | Reverse primer | | GCG ACG TCA TCG GTA AAT ACC A | | 23 |
| gyrA | Probe | FAM | TGT CGT AAA/ZEN/CTG CGG AA | Iowa Black | 24 |
| CT | Forward primer | | CATGAAAACTCGTTCCGAA ATAGAA | | 25 |
| CT | Reverse primer | | TCAGAGCTTTACCTAACAA CGCATA | | 26 |
| CT | Probe | FAM | TCGCATGCAAGATATCGA | BHQ-1 | 27 |

RT-PCR reactions including multiplexed detection of SARS-CoV-2 and control RNA as well as detection of SARS-CoV-2 and Influenza A and B on an assay cartridge were run for reverse transcription at 50° C. for 2 minutes and 50 cycles with temperature targets of 2 seconds denaturation at 102° C. followed by 2 seconds annealing at 50° C.

RT-PCR reactions including detecting SARS-CoV-2 N1 target were run for reverse transcription at 50° C. for 10 minutes and 50 cycles with temperature targets of 5 seconds denaturation at 95° C. followed by 20 seconds annealing at 60° C.

Finally, PCR reactions for detecting NG opa and gyrA target were run for 50 cycles with temperature targets of 5 seconds denaturation at 95° C. followed by 20 seconds annealing at 60° C.

Results and Discussion

One of the major challenges of diagnostic testing and genetic screening is a lack of easy and affordable methods to process and screen samples for a multitude of biomarkers in a timely manner. Current solutions rely heavily on tedious manual processing or expensive and complex fluidic handling instruments. To overcome this challenge, we have developed a sequential elution technique where magnetic particles simultaneously streamline analyte concentration and purification with direct aliquoting into multiple separate assay reagents. Sequential magnetic particle elution implemented in automated magnetofluidic assay cartridges provides integrated multiplexed detection directly from an unprocessed sample input. The elution of analytes off functionalized substrates and particles is a dynamic process in which an equilibrium is reached between the association rate of analyte binding to the particles ($K_A$) and dissociation rate of analytes released into solution ($K_D$) (FIG. 5B). The equilibrium state of the particles in elution buffer does not release all bound analytes, therefore multiple elution steps are possible wherein a portion of captured analytes may be eluted first into one assay reagent followed by sequential elution into a series of assay reagents for highly multiplexed testing with straightforward magnetic transfer.

The methods of multiple elution easily broaden the detection capability from a single PCR reaction into two PCR reactions. As a result, a negative swab sample spiked with SARS-CoV-2 RNA on the cartridge can be detected of infectious agents and internal control from a single source of specimen in the assay cartridge (FIG. 6A-C). The examples demonstrated the utility of sequential elution method for enabling multiplexed detection of analytes from a single specimen input without the need of additional fluorescent channel or complex instrumentation for valving and fluid manipulation. Furthermore, results of testing a single specimen against SARS-CoV-2 and 2 other respiratory viral infections influenza A/B on the magnetofluidic device also suggests the capability of multiplexing detection for providing a more streamlined and comprehensive report of a patient's infectious state for rapid linkage to targeted treatment (FIG. 7A-C).

The sequential elution methods can also achieve a higher degree of multiplexing. As a demonstration, this method has successfully eluted the analytes into PCR mix amplifying NG's opa and gyrA gene in 6 sequential elutions (FIG. 8A). All of the PCR assays were able to detect sufficient target signal (FIGS. 8B and C). Furthermore, the undetectable gyrA signal in the PCR assay reagent amplifying opa gene vice-versa showed there was no crosstalk between each elution, which indicates that the beads are able to serve as a carrier for sample DNA and move it from one assay reagent to another without interfering carryover from the previous assay. All the PCR assay reagents were able to detect the presence of either opa or gyrA gene, which implies the partial elution of the analyte into six individual assay reagents successfully. Furthermore, the undetectable gyrA signal in the PCR assay reagent amplifying opa gene and the undetectable opa signal in the PCR assay reagent amplifying gyrA gene showed there was no crosstalk between each elution, which indicates although the beads are able to serve as a carrier for sample DNA and move from one assay reagent to another, it will not carryover assay oligo from previous assay or interfere the downstream assay reactions.

Figure 10:
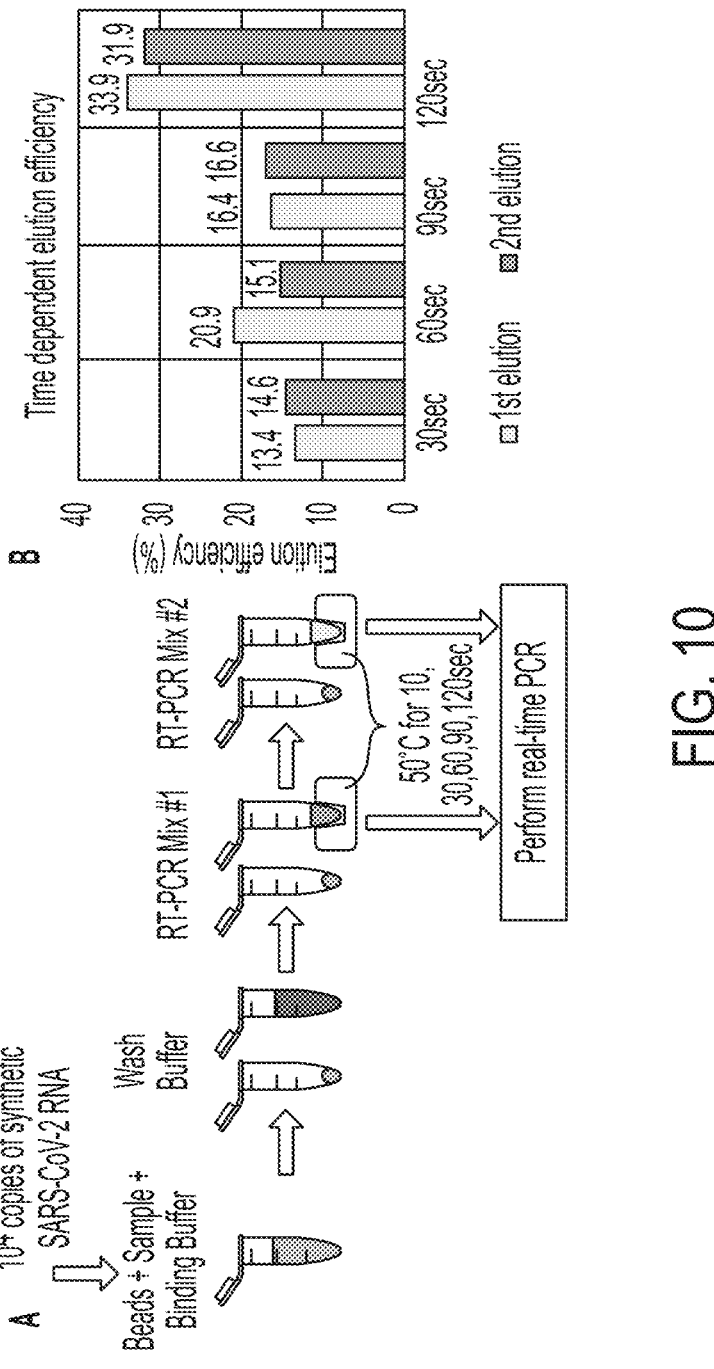
FIG. 10 (panels A and B) schematically depict time-mediated elution control according to some embodiments. (A) $10^4$ copies of synthetic SARS-CoV-2 RNA were concentrated by the magnetic beads and eluted sequentially into two separate RT-PCR mix (#1 and #2). In each group, the elution was performed at 50° C. for 30, 60, 90, or 120 seconds. (B) Elution efficiency was calculated as 100 * detected copies number (calculated based on standard curve in the same PCR plate) divided by $10^4$ copies. A trend of increment of eluted RNA copy number indicates the elution efficiency can be modulated with the elution duration.

The sequential elution method has also shown controllable release of analytes utilizing elution temperature and elution incubation time. The temperature-controlled elution efficiency was evaluated by eluting analytes into assay buffers at varying temperature (FIG. 9A). With elution at higher temperature, the detected N1 gene was increasing except for elution at 70° C., where the high temperature inactivated reverse transcription enzyme resulting in delayed Ct (FIG. 9B). The result showed that an elevated temperature encourages higher release of analytes from the magnetic particles. Another factor that contributes to the difference in elution efficiency is the elution time. The total number of eluted analytes off the particles is proportional to the elution time before the dynamic process reaches its equilibrium state; therefore, the longer incubation period allows more analytes eluted off the particles. A clear increment of eluted RNA with a longer incubation time indicated the partial elution efficiency is elution time-dependent (FIG. 10).

Figure 11:
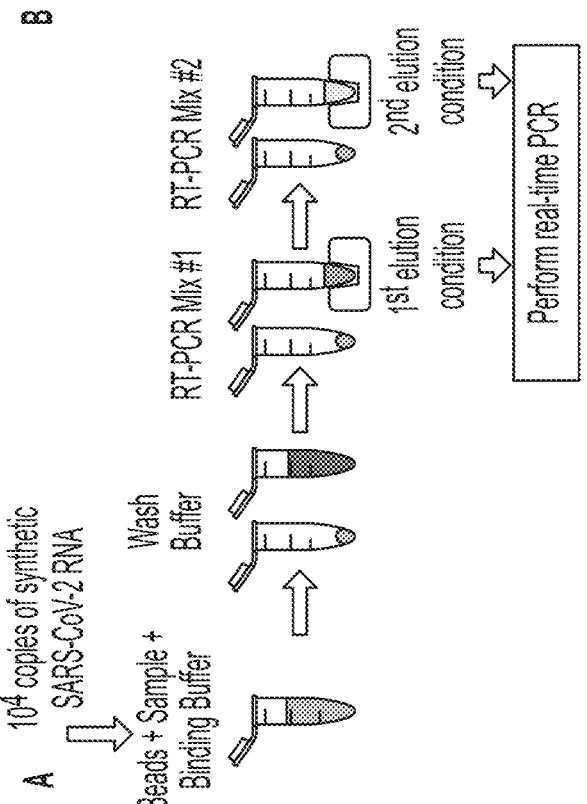
FIG. 11 (panels A and B) schematically depicts tunable partial elution with time and temperature modulation according to some embodiments. (A) $10^4$ copies of synthetic SARS-CoV-2 RNA were concentrated by the magnetic beads and eluted sequentially into two separate RT-PCR mix (#1 and #2). In each group, the first and second elution were shown in (B), with a total of five different sets. Elution efficiency for each elution was color-coded—more eluted copy number was grey, and less eluted copy number was white (no shading). When the elution condition was 60° C. for 2 minutes, the elution efficiency was as high as 30~40%. On the other hand, when the elution condition was 50° C. for 10 seconds, the elution efficiency was ~10%. The results showed that the elution efficiency was strongly related to the elution condition.

To permit sufficient analytes eluted in subsequent, multiple biochemical reaction assay, a controllable elution efficiency in each elute is necessary to ensure the balance between sufficient analytes get eluted and sufficient analytes remains on the beads for future elution. By controlling the temperature during elution and time the elution process lasts, the elution efficiency could be manipulated based on the needs. The controllable elution efficiency was demonstrated by elution into 2 RT-PCR mixtures with 5 sets of elution conditions (FIG. 11A). The results suggest elution at higher temperature and longer incubation time produce the strongest release of analytes into the assay for maximizing assay sensitivity, while elution at lower temperatures for a shorter time span, elution release was only ~10% of the analyte (FIG. 11B). The partial elution methods can be controlled to achieve the desired elution efficiency for expanding the number of assays while maintaining a consistent level of assay sensitivity.

To demonstrate the potential of increasing throughput of sequential elution and its universally applicability, the sequential elution method was automated by a commercially available robotic liquid handling system. A custom protocol for performing sequential elution from individual nucleic acid samples have been demonstrated for use on the epMotion 5075 system. Here we present the automated sequential elution by successfully eluting the DNA into PCR buffer amplifying CT DNA in 8 sequential elution, followed by real-time PCR by the benchtop real time PCR machine. The results showed that all the PCR reagents were able to detect the presence of CT DNA (FIG. 12B, 12C), which implies the partial elution of the analyte into 8 individual elution buffers was successful. Furthermore, this protocol was demonstrated to be compatible with magnetic beads from multiple vendors.

CONCLUSIONS

To achieve multiplexed biochemical reactions in an automated format without bulky and complex instrumentation, the methods described herein provide a streamlined workflow for combining analyte purification and aliquoting for achieving highly multiplexed biochemical reactions that can be implemented for automation in a compact and miniaturized instrument. The method has shown direct implementation into an on-demand magnetofluidic assay cartridge for significantly improved multiplexed detection capability. The controllable manner of the sequential elution is envisioned to be further utilized for expanding the multiplexing capability magnetofluidic cartridges while maintaining minimal instrumentation complexity, footprint, and cost.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, devices, systems, computer readable media, and/or component parts or other aspects thereof can be used in various combinations. All patents, patent applications, websites, other publications or documents, and the like cited herein are incorporated by reference in their entirety for all purposes to the same extent as if each individual item were specifically and individually indicated to be so incorporated by reference.

What is claimed is:

1. A method of detecting multiple biomolecules in a sample comprising a first biomolecule species and a second biomolecule species using a magnetofluidic cartridge comprising a sample inlet well, a first sample analysis well, and a second sample analysis well, wherein the first sample analysis well fluidly communicates with the sample inlet well and the second sample analysis well fluidly communicates with the first sample analysis well, the method comprising:

contacting, in the sample inlet, a plurality of magnetic particles and an aliquot of the sample such that the first biomolecule species and the second biomolecule bind to the plurality of magnetic particles and produce a first bound biomolecule species and a second bound biomolecule species;

moving the first bound biomolecule and the second bound biomolecule from the sample inlet well to the first sample analysis well using at least one magnet;

producing a first unbound biomolecule species in the first sample analysis well by eluting a portion of the first bound biomolecule species from the plurality of magnetic particles;

moving the remainder of the first bound biomolecule species and the second bound biomolecule species from the first sample analysis well to the second sample analysis using the at least one magnet;

producing a second unbound biomolecule species in the second sample analysis well by eluting a portion of the second bound biomolecule species from the plurality of magnetic particles;

detecting, in the first sample analysis well, the first unbound first biomolecule species or a derivative thereof or both; and detecting, in the second sample analysis, the second unbound biomolecule species or a derivative thereof or both.

2. The method of claim 1, further comprising washing the first bound biomolecule species and the second bound biomolecule species prior to the eluting the portion of the first bound biomolecule species from the plurality of magnetic particles or the eluting the portion of the second bound biomolecule species from the plurality of magnetic particles.

3. The method of claim 1 wherein the magnetofluidic cartridge further comprises:

a top layer;

a bottom layer spaced apart from the top layer in a substantial parallel orientation with respect to the top layer, which bottom layer including a bottom layer surface and defining a plurality of wells protruding from the bottom layer surface, wherein the plurality of wells comprises the sample inlet well, the first sample analysis well and the second sample analysis well;

a spacer layer operably connected to the top layer and the bottom layer;

a channel defined by the top layer, the bottom layer, and the spacer layer, which channel fluidly communicates with the plurality of wells;

at least one port disposed through the top layer and proximal to the sample inlet well, which at least one port fluidly communicates with the channel;

a sealing mechanism operably connected to the top layer, which sealing mechanism is configured to seal the port in a closed position;

the plurality of magnetic particles disposed in the sample inlet well; and a different processing reagent disposed in each sample analysis well of the plurality of sample analysis wells.

4. The method of claim 1 wherein the eluting the portion of the first bound biomolecule species from the plurality of magnetic particles and the eluting the portion of the second bound biomolecule species from the plurality of magnetic particles comprise tuning one or more elution conditions.

5. The method of claim 1 wherein the one or more elution conditions comprise one or more defined parameters selected from the group consisting of:

a temperature, a duration, a buffer composition, a reaction mixture composition, and a pH level.

6. The method of claim 1, wherein the first biomolecule species comprises a first locus of a genomic DNA or a first variant of a genetic locus and the second biomolecule species comprises a second locus of the genomic DNA or a second variant of the genetic locus, wherein the second locus is different from the first locus and the first variant is different from the second variant.

\*  \*  \*  \*  \*

SEQUENCE LISTING

```
<160> NUMBER OF SEQ ID NOS: 27

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaccccaaaa tcagcgaaat                                               20

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tctggttact gccagttgaa tctg                                         24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
accccgcatt acgtttggtg gacc                                         24

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttacaaacat tggccgcaaa                                               20

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcgcgacatt ccgaagaa                                                18

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
acaatttgcc cccagcgctt cag                                          23
```

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaatacggtg gattaaacaa aagcaa                                          26

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccagcaatag ctccgaagaa a                                               21

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
cacccatatt gggcaatttc ctatggc                                         27

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cttctaaccg aggtcgaaac gta                                             23

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggtgacagga ttggtcttgt cttta                                           25

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
tcaggccccc tcaaagccga g                                               21

-continued

```
<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tacaacaccc caacatcttc ga                                            22

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggaagttcac cggcgtcat                                                19

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
cgggcgtggc aggtcttccc                                               20

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agatttggac ctgcgagcg                                                19

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gagcggctgt ctccacaagt                                               20

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
ttctgacctg aaggctctgc gcg                                           23
```

```
<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttgaaacacc gcccggaa                                                         18

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tttcggctcc ttattcggtt taa                                                   23

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
ccgatataat ccgtccttca acatcag                                               27

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ttgcgccata cggacgat                                                         18

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gcgacgtcat cggtaaatac ca                                                    22

<210> SEQ ID NO 24

<400> SEQUENCE: 24

000

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 25
catgaaaact cgttccgaaa tagaa                                          25

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tcagagcttt acctaacaac gcata                                          25

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
tcgcatgcaa gatatcga                                                  18
```